US012409291B2

(12) United States Patent
Bechtel et al.

(10) Patent No.: US 12,409,291 B2
(45) Date of Patent: Sep. 9, 2025

(54) ADJUSTABLE FOREHEAD SUPPORT FOR A MASK

(71) Applicant: Loewenstein Medical Technology S.A., Luxembourg (LU)

(72) Inventors: Martin Bechtel, Winsen/Luhe (DE); Arnold Frerichs, Buxtehude (DE); Joachim Gardein, Tenerife/Canary Islands (ES)

(73) Assignee: LOEWENSTEIN MEDICAL TECHNOLOGY S.A., Luxembourg (LU)

(*) Notice: Subject to any disclaimer, the term of this patent is extended or adjusted under 35 U.S.C. 154(b) by 771 days.

(21) Appl. No.: 17/658,321

(22) Filed: Apr. 7, 2022

(65) Prior Publication Data
US 2022/0323703 A1    Oct. 13, 2022

(30) Foreign Application Priority Data

Apr. 9, 2021 (DE) .......................... 102021001836.2

(51) Int. Cl.
A61M 16/06 (2006.01)
(52) U.S. Cl.
CPC .... A61M 16/0655 (2014.02); A61M 16/0638 (2014.02); A61M 16/0683 (2013.01); A61M 2202/0208 (2013.01)

(58) Field of Classification Search
CPC .......... A61M 16/0633; A61M 16/0644; A61M 16/0655; A61M 16/0638
See application file for complete search history.

(56) References Cited

U.S. PATENT DOCUMENTS

| 2011/0126838 A1 | 6/2011 | Alberici et al. |
| 2012/0111333 A1* | 5/2012 | Eifler ................ A61M 16/0638 128/205.25 |
| 2014/0000617 A1 | 1/2014 | Rothermel et al. |
| 2018/0133426 A1 | 5/2018 | Hallett et al. |

FOREIGN PATENT DOCUMENTS

| EP | 2329858 A1 | 6/2011 |
| WO | 2010133218 A2 | 11/2010 |
| WO | 2016197195 A1 | 12/2016 |

* cited by examiner

Primary Examiner — Margaret M Luarca
(74) Attorney, Agent, or Firm — Abel Schillinger, LLP

(57) ABSTRACT

Forehead support adjuster for a mask, wherein the forehead support adjuster comprises at least a forehead support, consisting of support arm and cushion holder, a connection element, a rail with at least one guide groove, and a slide element, and wherein the slide element has at least one slide plate, at least one tenon and a guide element, wherein the at least one tenon is mounted rotatably and slidably in the at least one guide groove of the rail, and wherein the slide element is movably connected to the support arm. The forehead support adjuster is configured such that a movement of the slide element along the rail leads to a pivoting of the forehead support about at least one pivot axis D.

20 Claims, 22 Drawing Sheets

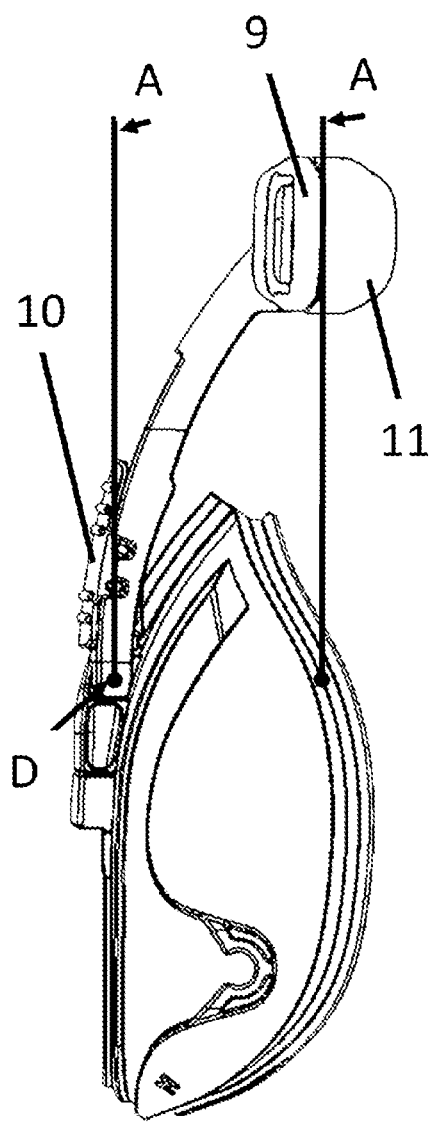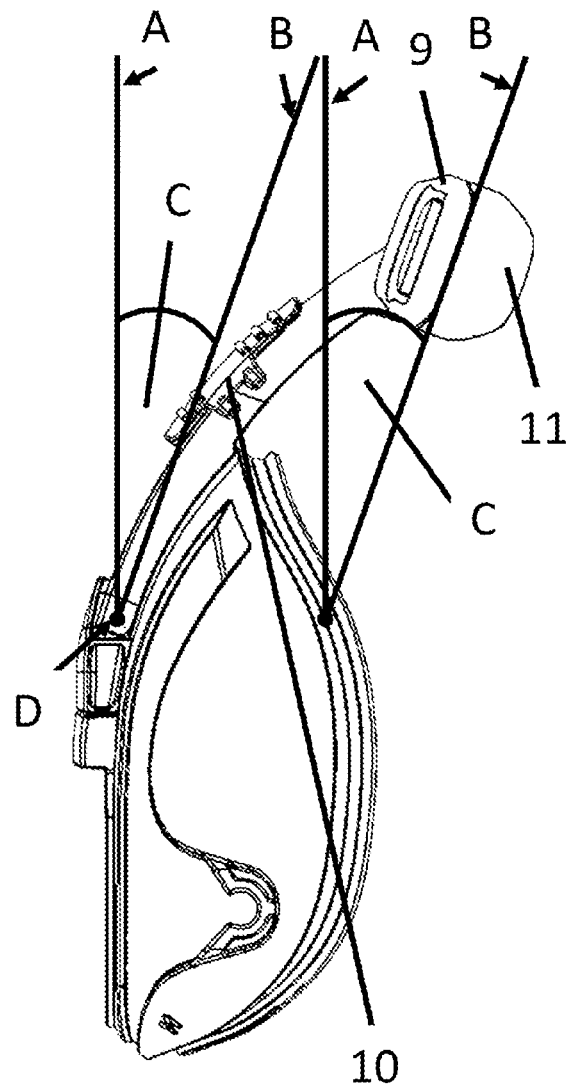
Figure 18A
Figure 18B
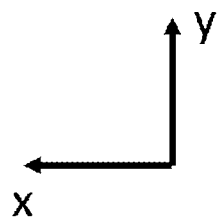

ADJUSTABLE FOREHEAD SUPPORT FOR A MASK

CROSS-REFERENCE TO RELATED APPLICATIONS

The present application claims priority under 35 U.S.C. § 119 of German Patent Application No. 102021001836.2, filed Apr. 9, 2021, the entire disclosure of which is expressly incorporated by reference herein.

BACKGROUND OF THE INVENTION

1. Field of the Invention

The invention relates to an adjustable forehead support for a mask.

2. Discussion of Background Information

To deliver respiratory gas from a ventilator to a patient, masks generally represent the interface between patient and ventilator. In addition to a gas-tight fit of the mask on the face of the patient, another important criterion is that the mask fits comfortably and precisely.

In addition to a mask cushion resting around the nose and/or mouth of the patient, the orientation on the face also plays an important role. The forehead support also affords a possibility of influencing the fit of the mask. Various forehead supports are known from the prior art, but they are often non-adjustable, move only along one direction or have a bulky and/or complicated construction.

It would therefore be advantageous to have available an adjustable forehead support which permits a secure and comfortable fit of the mask.

SUMMARY OF THE INVENTION

In a first aspect, the invention relates to a forehead support adjuster for a mask, wherein the forehead support adjuster comprises at least a forehead support, consisting of support arm and cushion holder, a connection element, a rail with at least one guide groove, and a slide element, and wherein the slide element has at least one slide plate, at least one tenon and a guide element, wherein the at least one tenon is mounted rotatably and slidably in the at least one guide groove of the rail, and wherein the slide element is movably connected to the support arm. The forehead support adjuster is characterized in that the forehead support adjuster is configured such that a movement of the slide element along the rail leads to a pivoting of the forehead support about at least one pivot axis D.

In some embodiments, the forehead support adjuster is characterized in that at least one inner wall is arranged on the slide plate, wherein the at least one tenon and the at least one guide element are arranged on the inner wall.

In some embodiments, the forehead support adjuster is characterized in that at least two notches are arranged in the rail, and a latching lug is arranged on at least one tenon, which latching lug can latch into the notches and can thereby fix a pivoting position.

In some embodiments, the forehead support adjuster is characterized in that the slide plate has, at two mutually opposite sides, respective wings which are substantially perpendicular to the slide plate.

In some embodiments, the forehead support adjuster is characterized in that the wings have at least in each case two subsidiary wings, wherein an interspace is present between the respective subsidiary wings.

In some embodiments, the forehead support adjuster is characterized in that the support arm has at least one carrier, which is rotatably connected to the connection element via at least one pin.

In some embodiments, the forehead support adjuster is characterized in that discrete markings for marking the pivoting position are arranged on at least one side of the at least one carrier, wherein the discrete markings are arranged such that at least one marking can be seen in the interspace between the subsidiary wings when the latching lug fixes the corresponding pivoting position.

In some embodiments, the forehead support adjuster is characterized in that the rail and the connection element are integrated in the mask body.

In some embodiments, the forehead support adjuster is characterized in that the support arm has at least two carriers, wherein the carriers are arranged parallel to each other and are connected to each other via connections.

In some embodiments, the forehead support adjuster is characterized in that the connections, together with the carriers, form a free space through which the slide element is at least partially plugged.

In some embodiments, the forehead support adjuster is characterized in that at least two inner walls are arranged on the slide plate and are arranged substantially perpendicular to the slide plate, and wherein tenons and the guide elements are arranged at the edges that lie opposite the slide plate.

In some embodiments, the forehead support adjuster is characterized in that the carriers are clamped between the slide plate and the guide elements.

In some embodiments, the forehead support adjuster is characterized in that the carriers of the support arm have at least one guide edge, along which the guide elements are guided.

In some embodiments, the forehead support adjuster is characterized in that the guide elements and tenons are arranged at a distance J from each other.

In some embodiments, the forehead support adjuster is characterized in that the guide edge and a top edge of the guide groove are at a distance K from each other when the guide edge and the guide groove extend parallel to each other.

In some embodiments, the forehead support adjuster is characterized in that the distance J is not equal to the distance K.

In some embodiments, the forehead support adjuster is characterized in that the distance J does not change during the movement of the slide element.

In some embodiments, the forehead support adjuster is characterized in that the guide groove has a curved or straight configuration, wherein a curved guide groove has a radius $R_1$.

In some embodiments, the forehead support adjuster is characterized in that the guide edge (30, 49) has a curved or straight configuration, wherein a curved guide edge (30, 49) has a radius $R_2$.

In some embodiments, the forehead support adjuster is characterized in that the radius $R_1$ is not equal to the radius $R_2$, and the ratio $R_2:R_1$ or $R_1:R_2$ lies in a range from 0.5 to 0.99, preferably 0.7 to 0.99, more preferably 0.75 to 0.985.

In some embodiments, the forehead support adjuster is characterized in that the radii $R_1$ and $R_2$ lie in a range between 7 cm and 15 cm, preferably between 9 cm and 11 cm.

In some embodiments, the forehead support adjuster is characterized in that the forehead support can be pivoted by a maximum pivoting angle C, wherein the maximum pivoting angle C lies between 100 and 40°, preferably between 150 and 25°.

In some embodiments, the forehead support adjuster is characterized in that the top edge of the guide groove lies on a circle K1 with the radius R1, and the guide edge lies on a circle K2 with the radius R2.

In some embodiments, the forehead support adjuster is characterized in that the pivot axis D always has the same relative position, i.e., lying inside or outside, with respect to the circles K1 and K2 when the maximum pivoting angle C is not exceeded.

In some embodiments, the forehead support adjuster is characterized in that the pivot axis D always lies outside the circle K2 and always inside the circle K1.

In some embodiments, the forehead support adjuster is characterized in that a sliding of the slide element along the rail in the direction of the cushion holder causes the support arm to approach the mask body.

In some embodiments, the forehead support adjuster is characterized in that the support arm transitions at one end into the cushion holder, wherein, at the end of the support arm lying opposite the end with the cushion holder, a peg is arranged on the connection, via which peg a closure piece is connected captively to the mask.

In some embodiments, the forehead support adjuster is characterized in that the cushion holder has a holder frame which, together with a holder center, forms a free space into which at least one cushion receiver protrudes from at least one side of the holder frame, in the direction of the holder center, and serves to receive a forehead cushion.

In some embodiments, the forehead support adjuster is characterized in that the tenons and guide elements are arranged and designed such that a sliding of the slide element leads to a movement of the tenons along the guide groove and a movement of the guide elements along the guide edge, wherein at the same time the forehead support is pivoted about the pivot axis D and the slide element is rotated about the tenons.

In a further aspect, the invention relates to a mask with a forehead support adjuster according to the invention, wherein a gas attachment is arranged between attachment and connection element.

In some embodiments, the mask is characterized in that the gas attachment is an attachment for an additional oxygen supply.

In some embodiments, the mask is characterized in that the gas attachment can be closed with a closure piece, wherein this closure piece is captively connected to the mask via a peg on the forehead support.

It is to be noted that the features individually presented in the claims can be combined with one another in any desired, technically meaningful way and show further refinements of the invention. The description additionally characterizes and specifies the invention in particular in conjunction with the figures.

It also is to be noted that an "and/or" conjunction used herein between two features, and linking them to each other, is always to be interpreted as meaning that in a first embodiment of the subject matter according to the invention only the first feature may be present, in a second embodiment only the second feature may be present, and in a third embodiment both the first and the second feature may be present.

A ventilator is to be understood as any appliance which supports the natural breathing of a user or patient, which takes over the ventilation of the user or living being (e.g., patient and/or neonate and/or premature baby) and/or which serves for respiration therapy and/or influences the respiration of the user or patient in some other way. This includes by way of example, but not exclusively, CPAP and BiPAP appliances, anesthesia appliances, respiration therapy appliances, ventilators (for use in hospitals, in non-hospital environments or in emergencies), high-flow therapy appliances and coughing machines. Ventilators can also be understood as diagnostic appliances for respiration. Diagnostic appliances can generally be used to detect medical and/or respiratory parameters of a living being. These also include appliances that are able to detect and optionally process medical parameters of patients in combination with respiration or only in relation to respiration.

Unless specifically stated otherwise, a mask can be understood as any peripheral conceived for interaction with a patient, in particular for therapeutic or diagnostic purposes. The mask can be a full-face mask, i.e., enclosing the nose and mouth, or a nose mask, i.e. a mask enclosing only the nose. Tracheal tubes and cannulas and so-called nasal cannulas can also be used as mask.

The fixing of a pivoting position by means of one or more latching lugs signifies releasable fixing. In the fixed position, a force generally has to be applied in order to move the slide element out of the fixed position.

BRIEF DESCRIPTION OF THE DRAWINGS

The invention is described in more detail by way of example with reference to FIGS. 1 to 22.

In the figures there is shown,
FIGS. 18A and 18B: a pivoting range of a forehead support

DETAILED DESCRIPTION OF EXEMPLARY EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

In the descriptions, it is assumed that the mask body as such has a fixed position and that the forehead support is moved by the forehead support adjuster. It is to be noted at this point that, conversely, the forehead support can be regarded as fixed and the mask body is moved by the forehead support adjuster. Ultimately, the forehead support adjuster provides a relative movement between mask body and forehead support.

Figure 1:
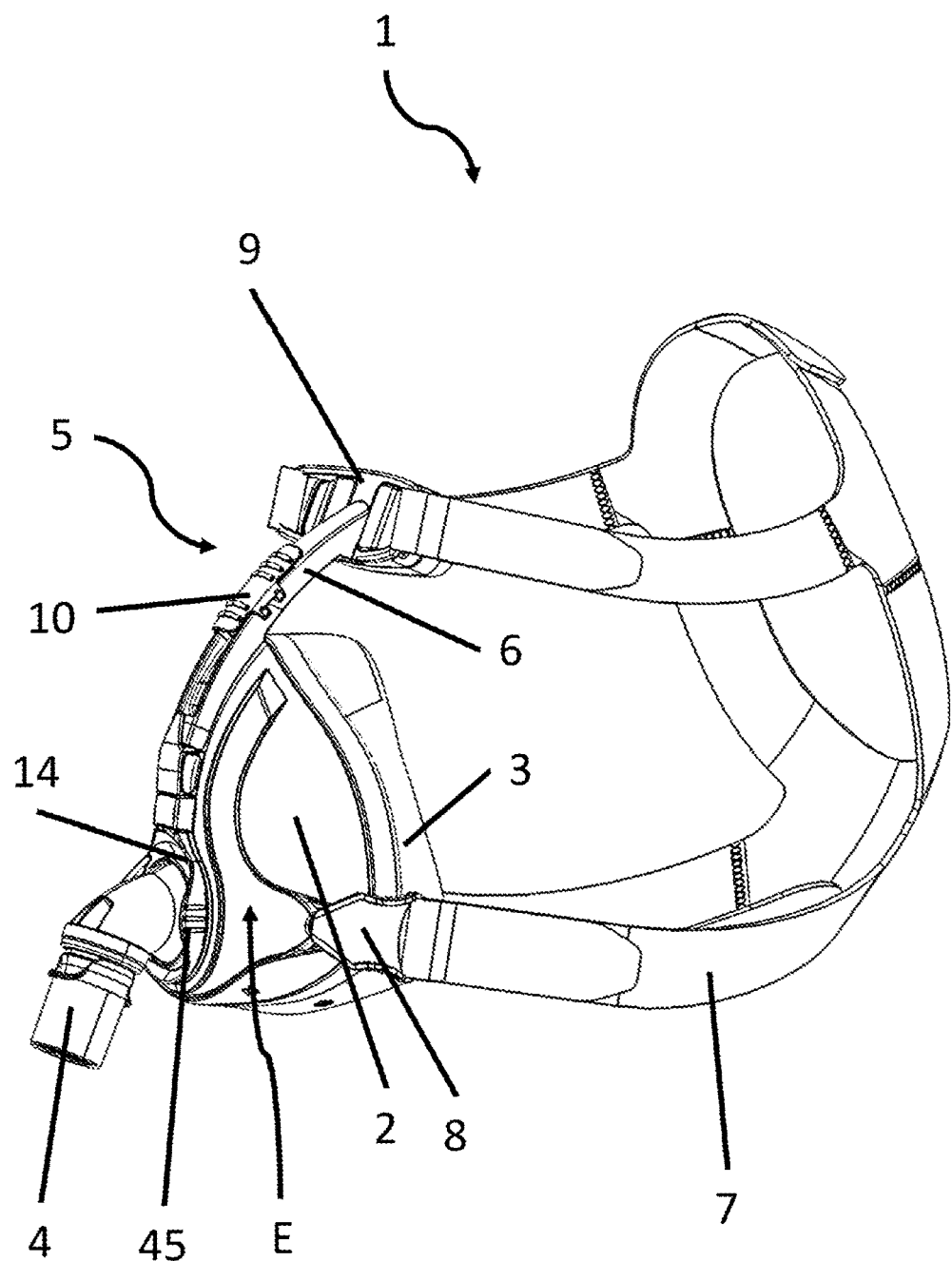
FIG. 1: a respiratory mask in a perspective view

FIG. 1 shows an exemplary embodiment of the forehead support adjuster according to the invention, consisting at least of forehead support 5, slide element 10, rail 17 (not visible in FIG. 1) and connection element 16 (not visible in FIG. 1), on a mask 1 which is designed, for example, for use with a ventilator. For this purpose, for example, a hose attachment 4 is connected to the mask body 2, and a hose system through which, for example, respiratory gas is conveyed to and from the patent can be connected to the hose attachment 4. The attachment 14 is, for example, configured such that different types of hose attachments 4 can be connected to the mask 1. In some embodiments, the attachment 14 also comprises exhalation structures through which respiratory gas can escape.

The forehead support adjuster serves to adapt the position of the forehead support 5 or the forehead cushion 11/cushion holder 9 relative to the mask body 2. According to the invention, the forehead support adjuster consists at least of the forehead support 5, a slide element 10, a rail 17, in which the slide element 10 is mounted rotatably and slidably, and a connection element 16 via which the forehead support 5 is connected rotatably or pivotably to the mask body 2. The position of the forehead cushion 11/cushion holder 9 relative to the mask body 2 is adapted by pivoting the forehead support 5 about a pivot axis D which is defined by the connection of the forehead support 5 to the connection element 16 by pins 27.

In some embodiments, it is also possible to have a plurality of pivot axes. For example, the pins 27 in the connection element 16 can assume different positions, such that a respective pivot axis can be found in each of the different positions. Moreover, the tenons 25 of the slide element 10 become a pivot axis through a movement between the different positions in the connection element 16.

The mask body 2 is generally shell-shaped with at least two openings, such that an inner side F and an outer side E of the mask body 2 can be distinguished. The inner side F lies in the inner space, i.e., in the shell-shaped mask body, which substantially encloses a volume. The outer side E of the mask body 2 accordingly lies outside the mask body.

Moreover, at least one head harness 7 is connected to the mask body 2. In the embodiment shown, the head harness 7 is for example designed in one piece, wherein a connection to the mask 1 is effected in the region of the mask body 2, here for example via harness clips 8, and configured via the cushion holder 9 of the forehead support 5. In addition to the one-piece head harness 7 shown, it is also conceivable to have a multi-part head harness 7. Thus, a part of the head harness 7 can be connected to the mask 1 only in the region of the mask body 2, and a further part of the head harness 7 only via the forehead support 5 (for example via the cushion holder 9).

For a gas-tight fit of the mask 1 on the face of a user, a face cushion 3 is also connected to the mask body 2. It will be noted at this point that in principle any type of face cushion 3 can be used. It is assumed here that a skilled person knows how the mask body 2 could accordingly be adapted to different face cushions 3 in terms of a connection to the mask body 2. In some embodiments, the forehead support adjuster according to the invention is also designed to be arranged and used in a mask 1, which constitutes a one-piece design of the mask body 2 with face cushion 3.

The forehead support 5 with forehead support adjuster is for example arranged externally, i.e., on the outer side E, on the mask body 2. The forehead support 5 can be divided here into the support arm 6 and the cushion holder 9. The cushion holder 9 serves for example to receive the forehead cushion 11 and optionally also the holder of a head harness 7. The support arm 6 constitutes a connection between cushion holder 9 and the mask body 2. The forehead support adjuster according to the invention allows the position of the cushion holder 9 to be adapted by pivoting of the forehead support 5 about a pivot axis D, which lies at the end of the support arm 6 opposite the cushion holder 9.

Figure 2:
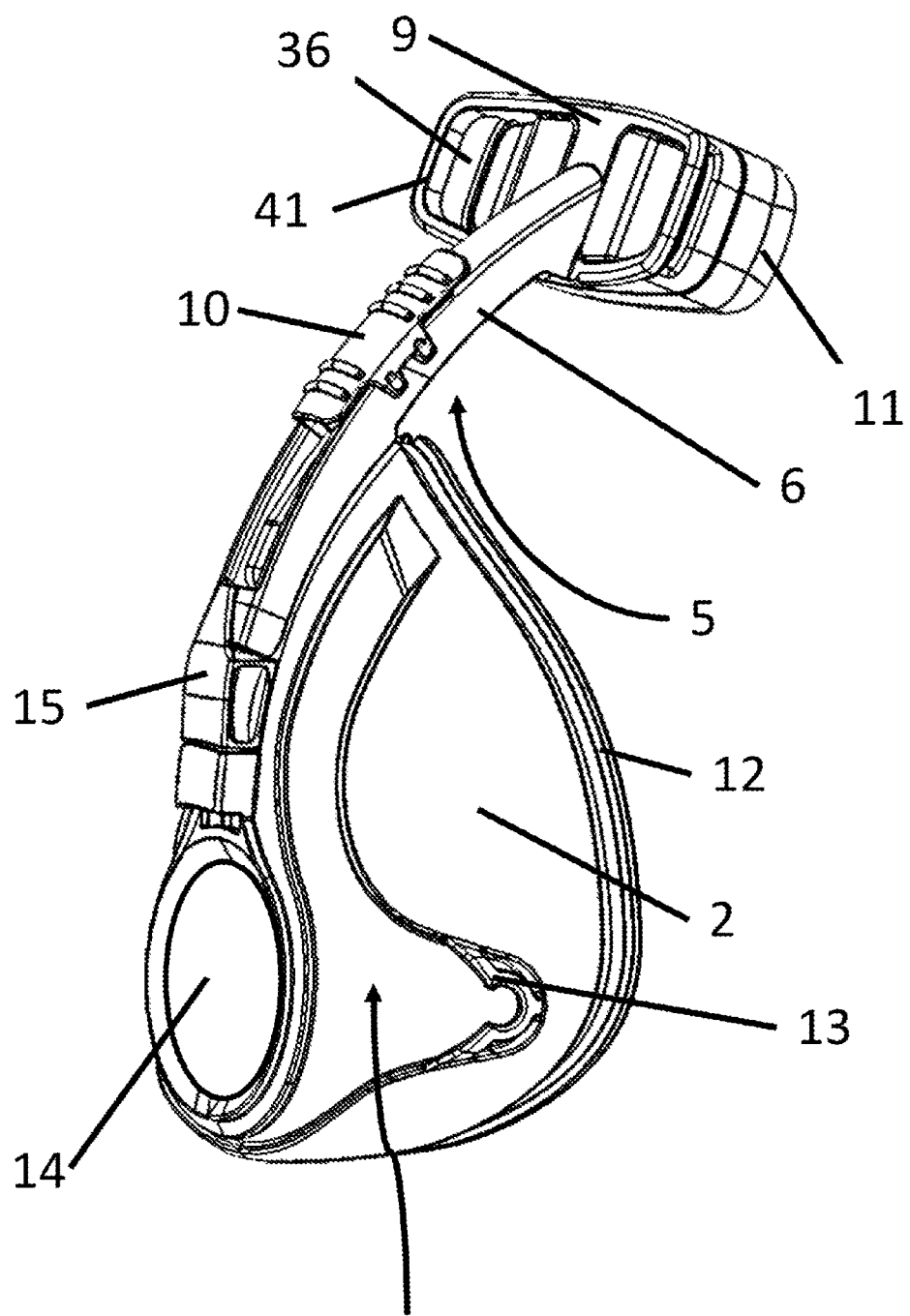
FIG. 2: a mask body with forehead support

FIG. 2 shows a perspective view of an exemplary embodiment of the mask body 2 with the forehead support adjuster. The mask body 2 has, for example, a cushion attachment 12 for connection to a face cushion 3, and an attachment 14, for example for connection to a hose attachment 4. In some embodiments, the attachment 14 can also be designed in such a way that, for example, a filter element can be attached, for example also without a hose system for delivery of respiratory gas. The part of the mask body 2 in which the attachment 14 is arranged can be regarded, for example, as a lower part of the mask. The mask body 2 usually has a mirror-symmetrical shape, with the mirror plane G running centrally through the mask body 2 (see FIG. 5). In particular, functional and cosmetic details can deviate entirely from the symmetry, for example asymmetrically arranged guide lines, for example for locking a hose attachment 4 in the attachment 14. The attachment 14 is for example arranged at the bottom, centrally in the mask body 2, such that the plane of symmetry G runs centrally through the attachment 14.

Clip holders 13, which can receive harness clips 8 with the head harness 7, are arranged laterally on the outside E of the mask body. For example, the harness clips 8 are clipped into the clip holder 13, wherein the harness clips 8 can rotate in at least one plane in the clip holder 13 and, if appropriate, also have a certain degree of freedom of movement. Alternatively (or in addition) to a combination of clip holder 13 and harness clips, other ways of holding the head harness 7 on the mask body 2 are also possible.

A closure piece 15, which closes an additional, optional gas attachment 18, is for example arranged above the attachment 14. The closure piece 15 is, for example, connected captively to the support arm 6. The closure piece 15 serves to close the gas attachment 18 when the latter is not required. In some embodiments, this gas attachment 18 is not arranged in the mask body 2, and therefore the closure piece 15 is not arranged.

The forehead support 5 is, as part of the forehead support adjuster, arranged above the closure piece 15 or the gas attachment 18 on the outside E of the mask body 2 but is not part of the mask body 2. At one end of the support arm 6, the forehead support 5 is connected pivotably to the mask body 2 via at least one connection element 16 of the mask body 2. Arranged at the other end of the support arm 6 is the cushion holder 9, which is designed on the one hand to receive at least one forehead cushion 11 and a head harness 7. The head harness 7 is guided around the harness receiver 41, for example through at least one gap 36 of the cushion receiver 9, and fixed. For example, the head harness 7 can be fixed by a kind of hook-and-loop closure.

The forehead support adjuster moreover comprises the slide element 10 which, by way of tenons 25, is connected to the mask body 2 so as to be rotatable and slidable in a rail 17 and also connected slidably to the support arm 6. By sliding of the slide element 10, the forehead support 5 is pivoted about the pivot axis D, which lies in the pins 27 connected to the connection element 26.

Figure 3:
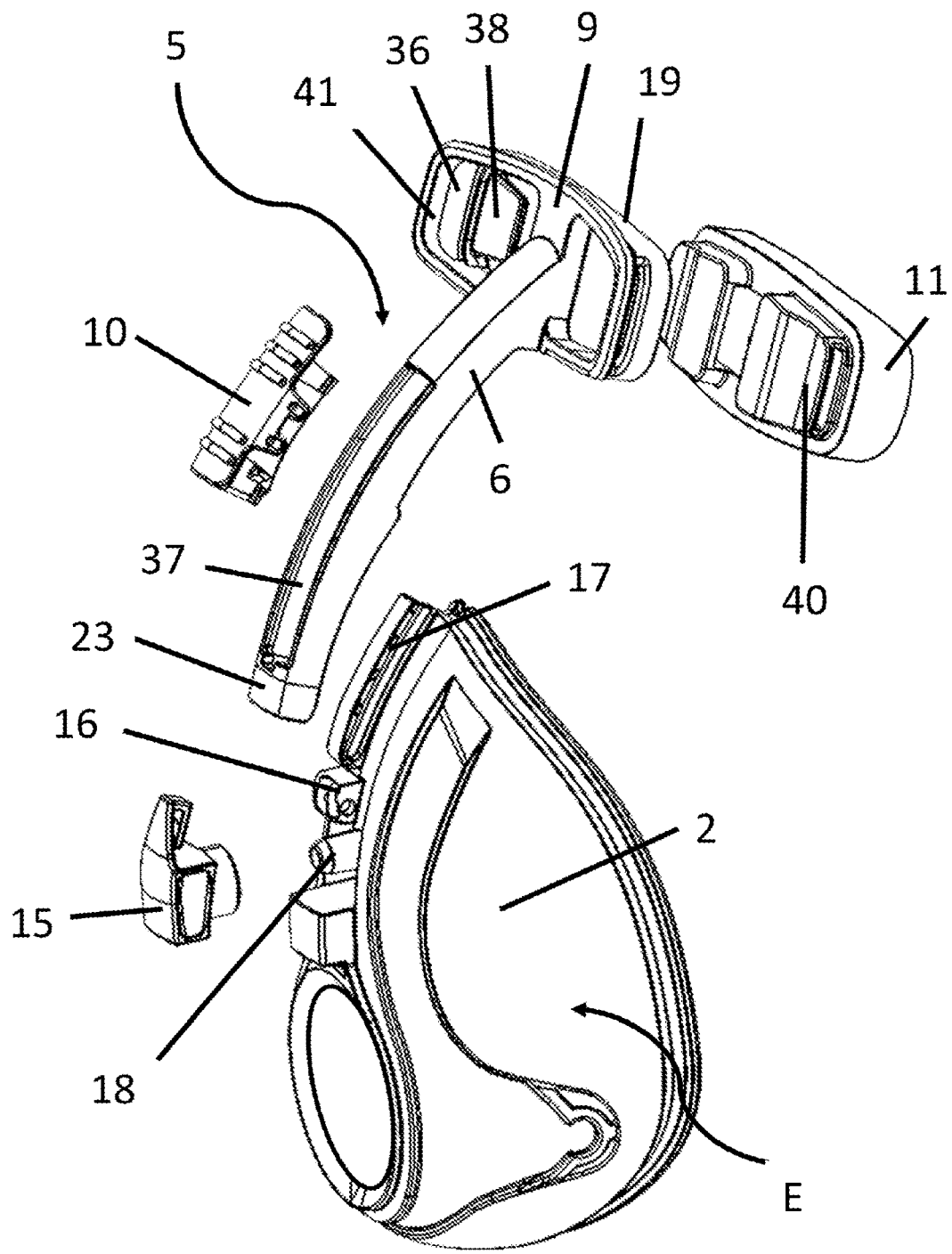
FIG. 3: a perspective exploded view of a mask body with forehead support
Figure 4:
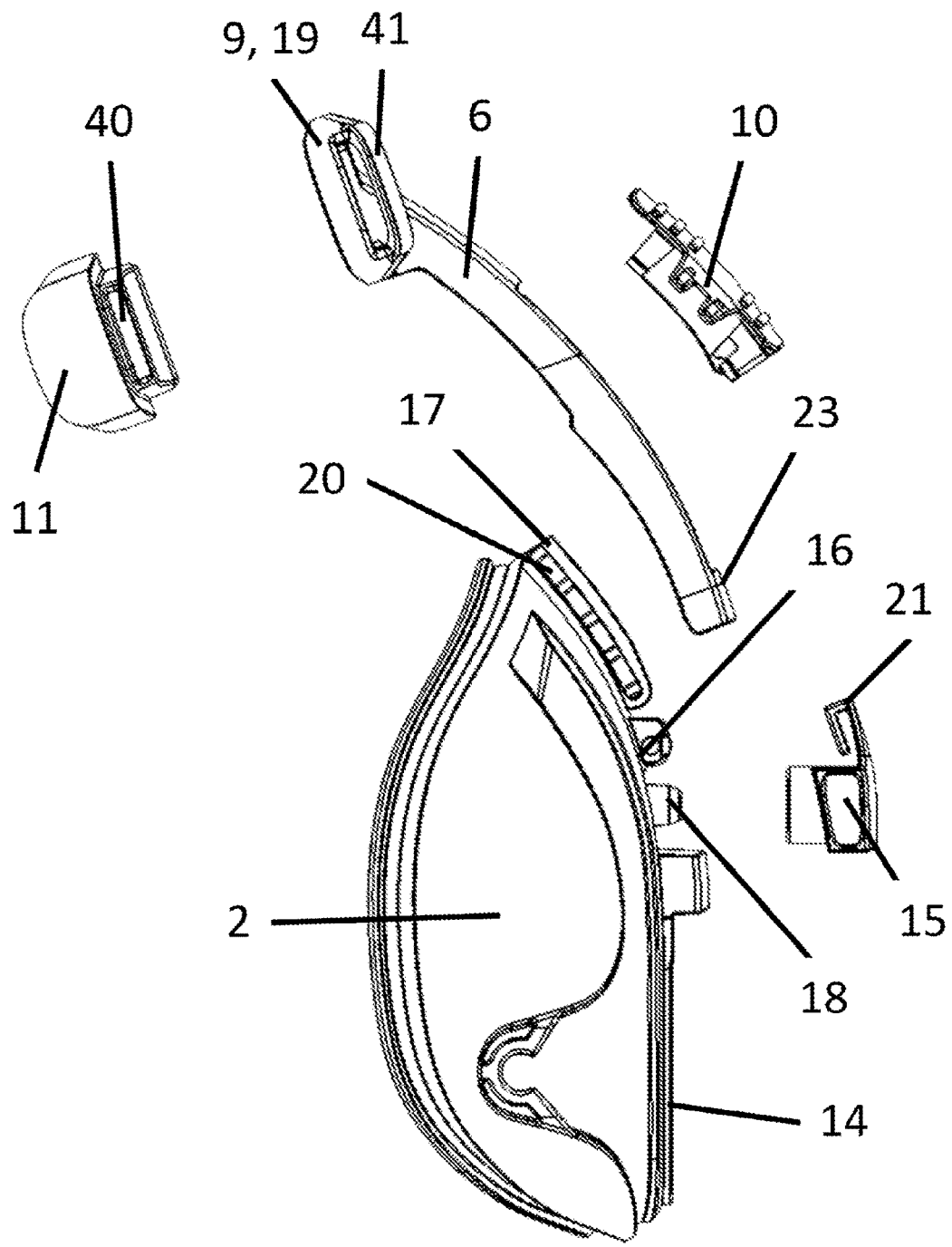
FIG. 4: an exploded side view of a mask body with forehead support
Figure 4:
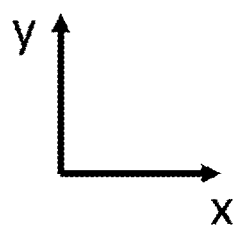

An exemplary embodiment of the forehead support adjuster is shown, with the mask body 2, in an exploded view in FIGS. 3 and 4. FIG. 3 shows a perspective view, FIG. 4 a side view.

Among other things, the following are formed and/or arranged on the outer side E of the mask body 2: the rail 17 for the rotatable and slidable connection to the slide element 10, a connection element 16 for the movable, rotatable connection to the support arm 6 of the forehead support 5, and the gas attachment 18 which can be closed by the closure piece 15. The rail 17 and/or the connection element 16 can, for example, be fitted onto the mask body 2 or can be part of the mask body 2. If rail 17 and/or connection element 16 are part of the mask body 2, they are materially connected to the mask body 2 and preferably produced in one piece. If the rail 17 and/or connection element 16 are fitted on, they are connected to the mask body for example by being plugged on, glued on and/or screwed on.

The cushion holder 9 is arranged at one end of the support arm 6 of the forehead support 5. The cushion holder 9 has a holder frame 19, from which the harness holder 41 starts. Between the harness holder 41 and the holder frame 19, there is a gap 36 through which the head harness 7 can be guided. Also formed on the cushion frame 19 are, for example, two cushion receivers 38 via which the pockets 40 of the forehead cushion 11 can be plugged in order to connect the forehead cushion 11 to the cushion holder 9. Alternatively, the pockets 40 can also be designed as a tab or tabs, in which case the tabs are each pulled through one of the cushion receivers 38.

At the end opposite the cushion holder 9, the support arm 6 is pivotably connected to the connection element 16. The connection to the connection element 16 at the same time constitutes the pivot axis D about which the support arm 6 or the forehead support 5 is pivotable. The support arm 6 moreover has a free space 37 through which the slide element 10 is at least partially inserted. The extent of the free space 37 determines the distance by which the slide element 10 is able to slide. In addition to the support arm 6, the slide element 10 is also connected to the rail 17. The slide element 10 is rotatably and slidably mounted inside the rail 17, such that a pivoting movement of the forehead support 5 is permitted by the sliding of the slide element 10.

Arranged on the closure piece 15 is, for example, a closure tab 21 with which the closure piece 15 can be connected captively to the mask 1 or the forehead support 5. For this purpose, the closure tab 21 has a hole, for example, through which a peg 39 of the support arm 6 can be plugged. This peg 39 is located, for example, in an interspace 35 of the connection element 16. The closure tab 21 is, for example, designed such that it can be placed around the connection 23 of the support arm 6 (see, for example, FIG. 9).

Figure 5:
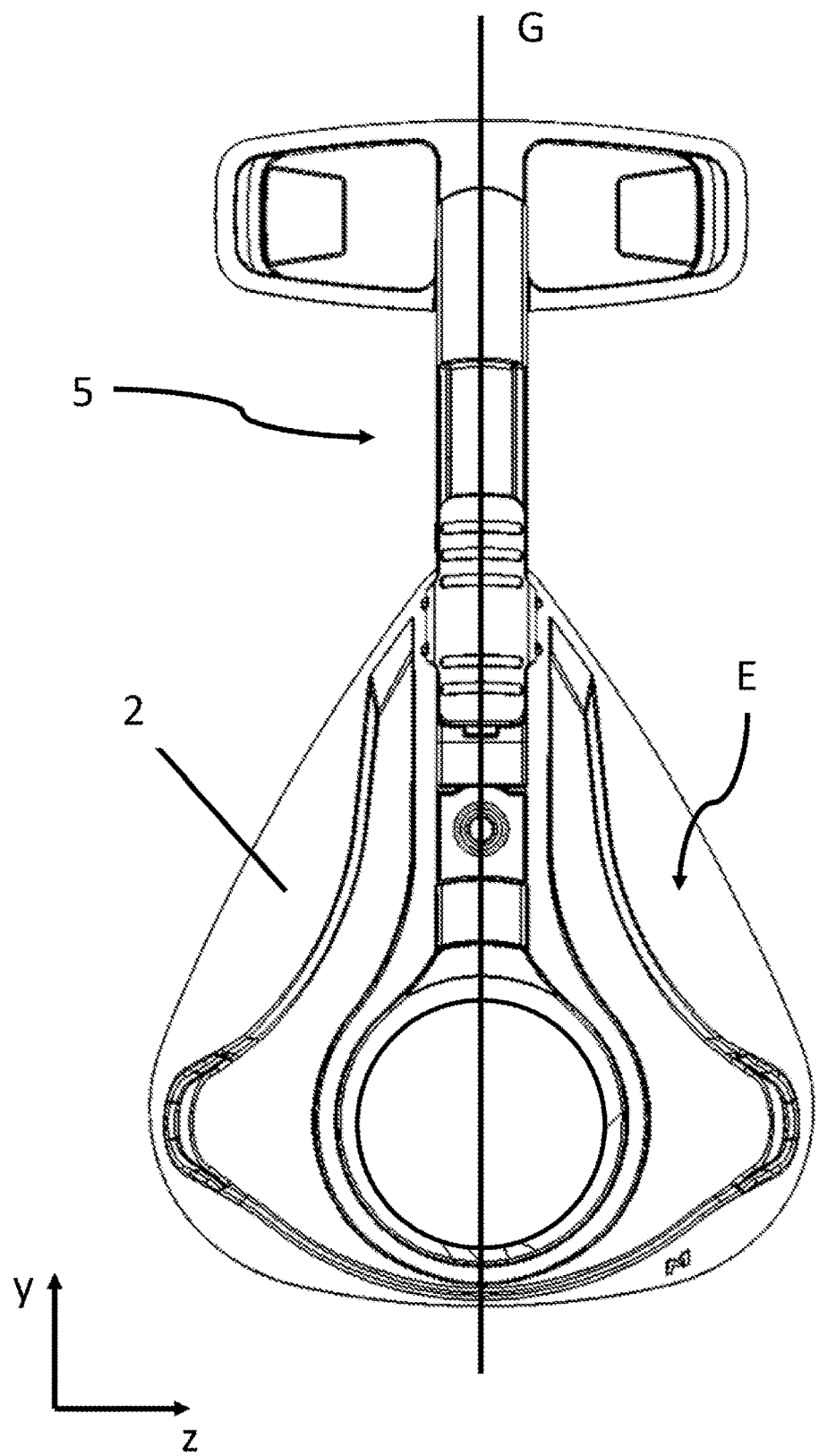
FIG. 5: a front view of a mask body with a forehead support adjuster, in order to illustrate the plane of symmetry

FIG. 5 shows the front view (along the x axis; FIG. 4) of an exemplary embodiment of the mask body 2 with forehead support adjuster and forehead support 5. It will be seen that the mask body 2 and also the forehead support 5 are substantially mirror-symmetrical. The plane of symmetry G runs centrally through the mask body 2 and the forehead support 5 and parallel to the plane spanned by the x axis and y axis (see FIG. 4). It will be noted that there is generally no perfect symmetry, and the respective mirror images may differ in a number of details, for example the design of the rail 17 of the mask body 2, which rail 17, in some embodiments, has notches 33 on one side in the guide groove 20. Moreover, the attachment 14 for example can also be designed such that asymmetrical elements are formed or various elements are arranged asymmetrically, for example in the guiding of the closure lock. Said elements, which can have an asymmetry, serve at this point only for explanatory purposes and do not in any way constitute a complete list of possible asymmetries.

Figure 6:
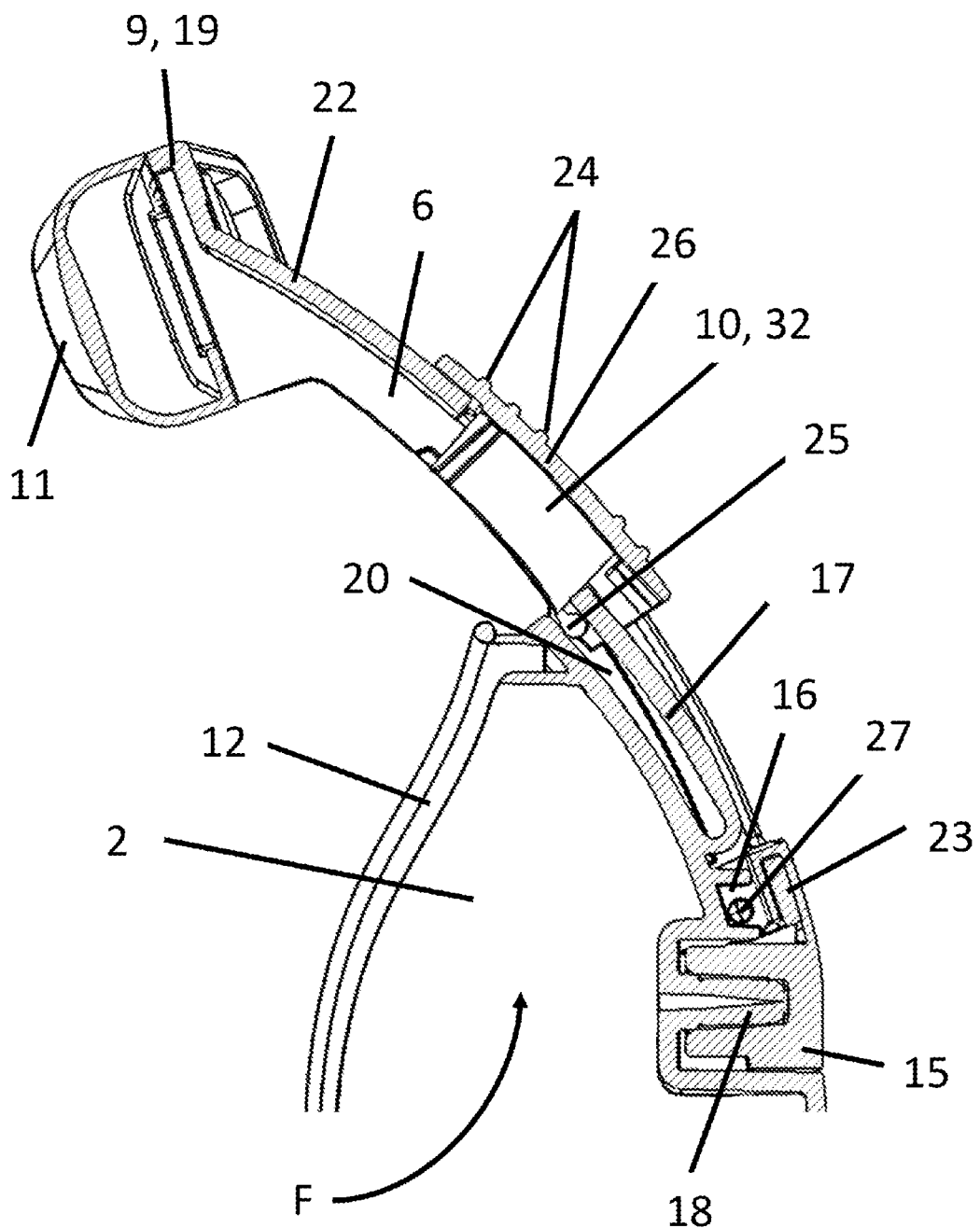
FIG. 6: a longitudinal section through forehead support and mask body

FIG. 6 shows a longitudinal section through an exemplary embodiment of the mask body 2 and of the forehead support adjuster, comprising among other things the forehead support 5 and the slide element 10. The section plane corresponds substantially to the plane of symmetry G; the section plane is slightly offset laterally (in the z direction; FIG. 5) such that the section is not precisely central.

The gas attachment 18, which produces a connection between the interior of the mask body 2, surrounded by the inner side F, and the exterior of the mask body 2, is closed by the closure piece 15 in the view shown in FIG. 6. The closure piece 15 is connected captively to the support arm 6, wherein the tab 21 is guided around the connection 23 at one end of the support arm 6 and pulled over the peg 39 (not shown in FIG. 6) which is arranged at the connection 23. The gas attachment 18 serves, for example, for additional introduction of oxygen or other gases into the interior of the mask. The gas attachment 18 is arranged, for example, between attachment 14 and connection element 16, as a result of which the gas attachment is located in the nose region when the mask 1 is being worn by a user.

The connection 23 extends for example over the connection element 16, to which the forehead support 5 is rotatably or pivotably connected via pins 27. The pins 27 thus at the same time constitute the pivot axis D about which the forehead support 5 is pivoted.

The rail 17 of the mask body 2 is arranged above the connection element 16 (y direction). The rail 17 has at least one guide groove 20 in which the tenons 25 of the slide element 10 are slidably and rotatably mounted. In some embodiments, the rail 17 has a wall 46 centrally in the z direction, such that a guide groove 20 is formed on both sides of the wall 46. The rail 17, or at least the guide groove 20, has a curved shape, for example, and has a radius R1. In some embodiments, this radius R1 substantially follows the shape of the mask body 2. In some embodiments, the radius R1 is independent of the shape of the mask. In some embodiments, the guide groove 20 is straight and/or follows a parabola and/or a free form. In some embodiments, the guide groove 20 can alternate between regions in which it is parabola-shaped, circularly curved and/or straight.

In some embodiments, the guide groove 20 is designed such that the pivot axis D lies on the arc or circle K1 with radius R1, which is described by the curved shape of the guide groove 20. In some embodiments, the pivot axis D also lies within the circle K1 with radius R1, on the circumference of which the guide groove 20 runs. The radius R1 measures, for example, between 7 and 15 cm, preferably between 9 and 11 cm.

The slide element 10 is connected movably to the mask body 2 via the tenons 25 which are mounted rotatably and slidably in the guide groove 20. The slide element 10 is thus able to slide in the rail 17, while at the same time a rotational movement is possible, for example in interaction with the forehead support 5. The tenons 25 are for example formed on inner walls 32 at a corner. Each inner wall 32 is formed with just one tenon 25, so that a rotatability in the rail 17 is possible. The tenons 25 lie for this reason on a common axis. The inner walls 32 start, for example, from a slide plate 26 which bears, for example, on the support arm 6 of the forehead support 5. To provide better grippability of the slide element 10, grip structures 24, for example, are formed among other things on the slide plate. These grip structures 24 are designed, for example, as sleeper-like elevations on the slide plate 26. Besides this design, further forms of the grip structures 24 are also possible, for example knobs, or in the form of a grip recess.

In some embodiments, the slide element 10 only has an inner wall, for example with a tenon 25 on both sides and guide elements 29 on at least one side.

The slide element 10 constitutes a binding member between forehead support 5 and mask body 2. The forehead support 5 is therefore connected to the mask body 2 both via the pins 27 in the connection element 16 and via the slide element 10. By virtue of the fact that the slide element 10 is mounted rotatably in the rail 17, but the slide plate 26 of the slide element 10 bears on the support arm 6 of the forehead support 5, a pivoting of the forehead support 5 is possible only when the slide element 10 is moved in the rail 17. A free pivoting of the forehead support 5, i.e. independently of the slide element 10, is prevented by the slide element 10.

At that end of the support arm 6 not connected to the connection element 16 via the pins 27, the support arm 6 transitions into the cushion holder 9. The distance by which the slide element 10 can be pushed is limited by the connection 22. This also prevents a situation where the slide element 10 is pushed out of the rail 17 and the forehead support 5 is freely rotatable about the pivot axis D.

Figure 7:
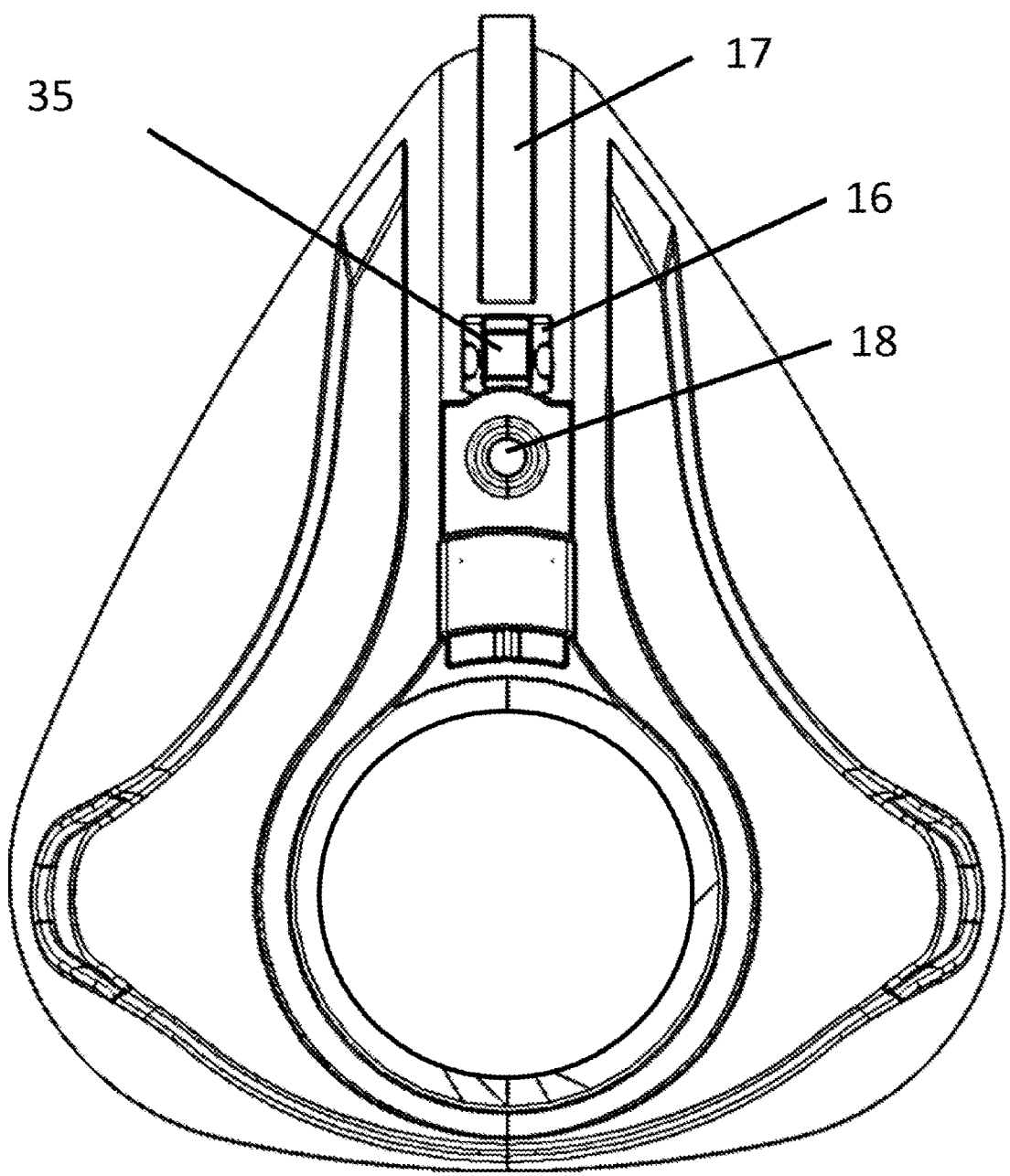
FIG. 7: a front view of a mask body

FIG. 7 shows an exemplary embodiment of the mask body 2 with the rail 17 and the connection element 16 in a front view. The rail 17 is arranged in the upper part of the mask body 2 (along the y axis above the gas attachment 18). The connection element 16 is arranged below the rail 17. The connection element 16 is composed, for example, of two walls, these walls each having an opening into which the pins 27 are inserted. In some embodiments, the pins 27 can also be arranged on the connection element 16 on the mask body 2, and the support arm 6 has the corresponding openings into which the pins are inserted. In addition, any rotatable types of connection between support arm 6 and mask body 2 are also conceivable. For example, both the support arm 6 and the connection element 16 can have openings through which a pin is inserted which rotatably fixes the forehead support 5 in the connection element 16.

Located between the walls of the connection element 16 there is, for example, an interspace 35 that provides room for receiving the peg 39.

Figure 8:
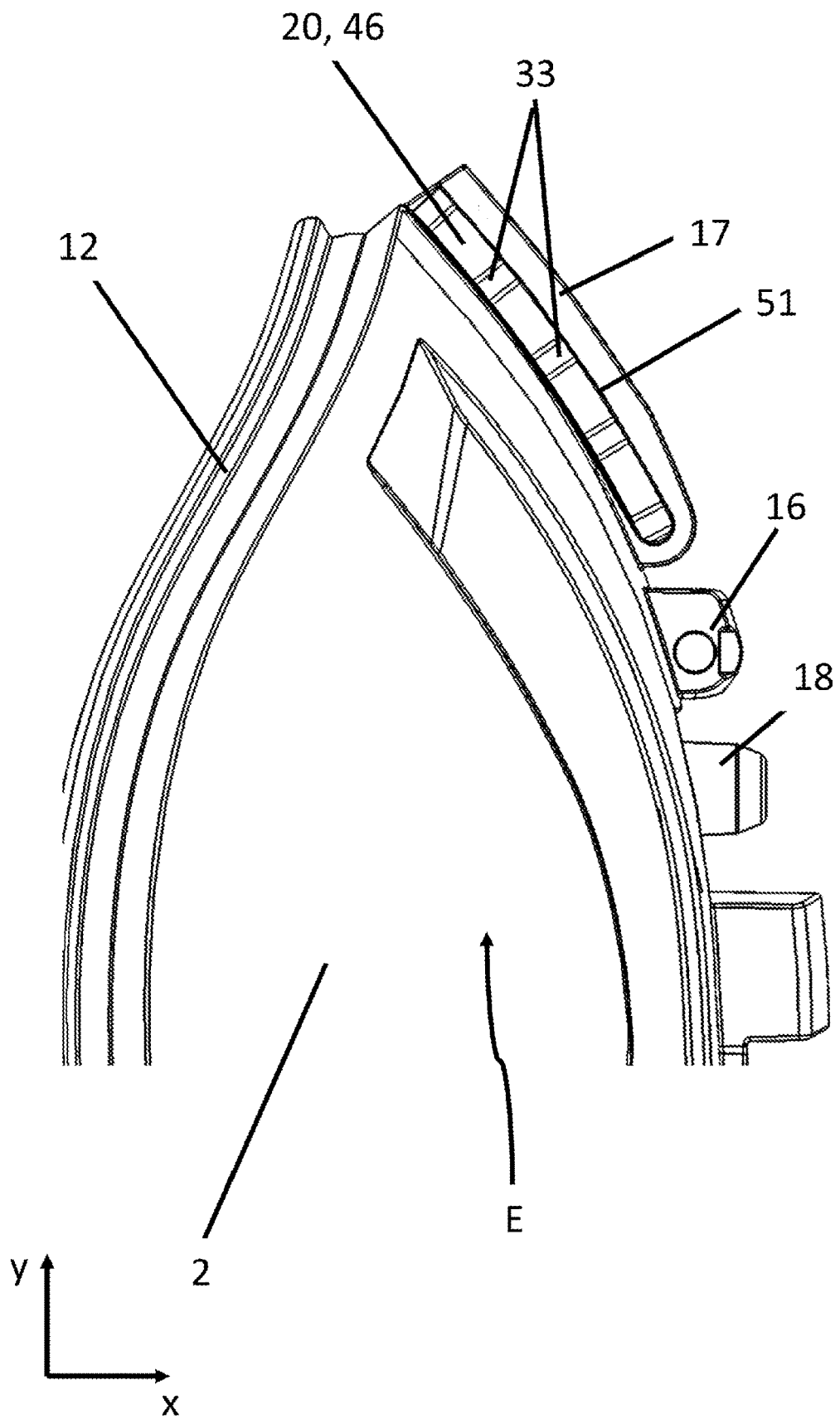
FIG. 8: a side view of a mask body

A side view of an exemplary embodiment of the mask body 2 is shown in FIG. 8. The rail 17 is at least partially integrated in the mask body 2. For example, the rail 17 has a wall 46 and accordingly has two guide grooves 20 on each side of the wall 46. Several notches 33, at least two thereof, are formed in the wall 46, at least on one side. Alternatively or in addition, the notches 33 can also be arranged on both sides of the wall 46. In some embodiments, an alternative or supplementary arrangement of the notches 33 in the top edge 51 of the rail 17 or in the side of the rail 17 opposite the top edge 51 is also possible. The slide element 10 is guided along the guide groove 20 with the tenons 25. A latching lug 34, which is formed on at least one of the tenons 25, can latch into the notches 33 of the guide groove 20 and thereby fix the set position of the forehead support 5. The latching lug 34 is here arranged on the tenon 25 such that latching into the notches 33 is possible. If the notches 33 are arranged for example in the top edge 51 of the rail 17, the latching lug 34 is formed for example on the corresponding side of the tenon 25. In some embodiments, the guide groove 20 has no notches, and the tenons 25 are also designed without latching lug 34. In some embodiments, latching points are also realized at other locations or not formed at all, such that the slide element 10 cannot latch in. The rail 17 or at least the guide groove 20 is curved and has a radius R1. In alternative or supplementary embodiments, the guide groove 20 has a linear shape or parabola shape and/or a combination between curved, straight and/or parabola-shaped.

Figure 9:
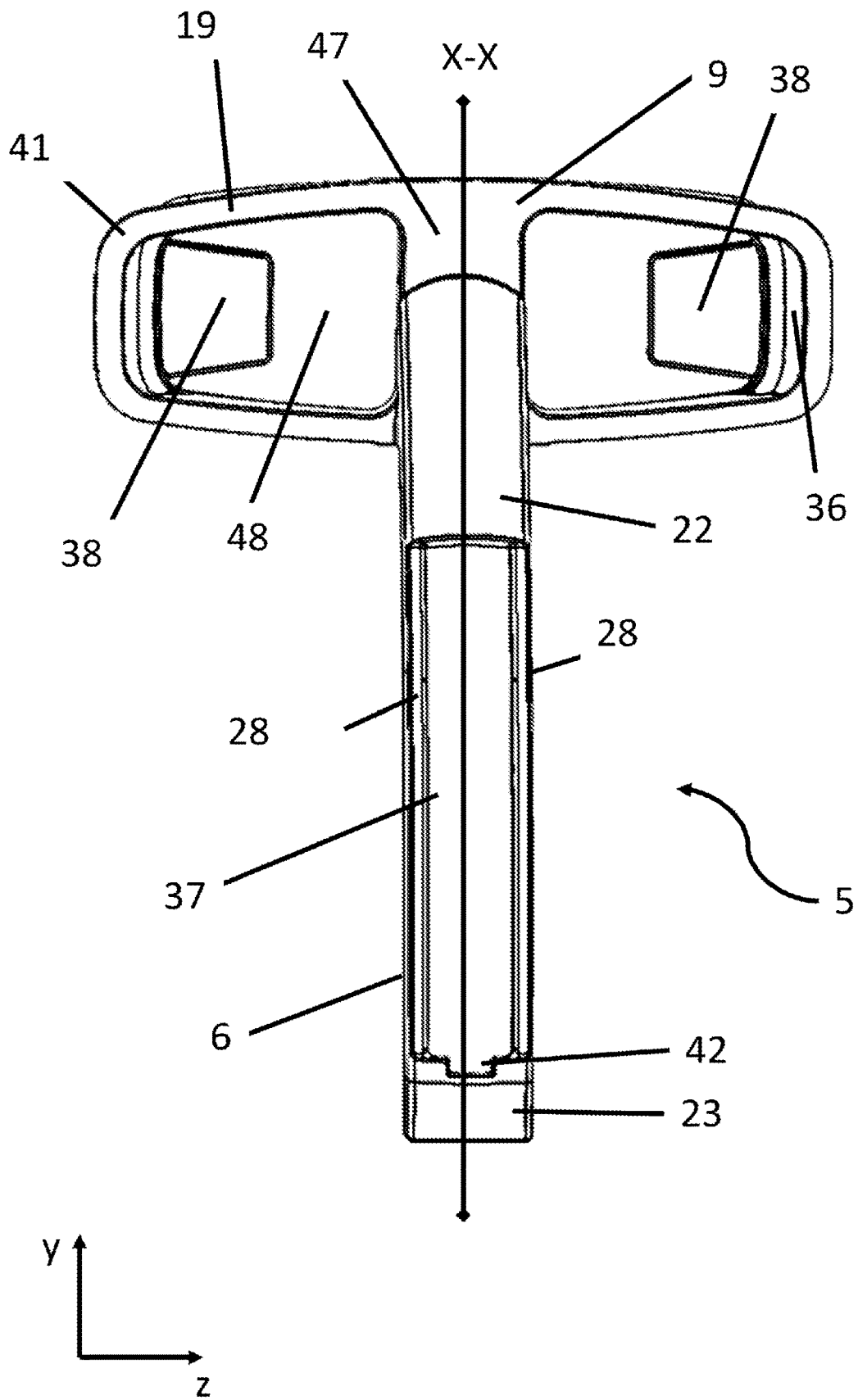
FIG. 9: a front view of a forehead support

An exemplary embodiment of the forehead support 5 is shown in FIG. 9 in a front view. The forehead support 5 can be roughly divided into the support arm 6 and the cushion holder 9, the support arm 6 transitioning at one end into the cushion holder 9. The cushion holder 9 begins, for example, at the place where the substantially curved support arm 6 ends at an edge. In addition to a curved shape, the support arm 6 can also be straight and/or parabola-shaped. From this edge, the cushion holder 9 widens to the sides among other things. The cushion holder 9 is rotated through 90° with respect to the support arm 6, as a result of which the front view of the forehead support 5 reveals what is substantially a T shape. For example, the cushion holder 9 thus has a width which is at least twice as great as the other dimensions. In some embodiments of the forehead support 5, the cushion holder 9 has other shapes. In the embodiment shown in the figures (at least FIGS. 1-5, 8, 9 and 18), the cushion holder 9 describes a rectangle in a front view, although it can also adopt all possible other shapes, for example a square, round or polygonal shape or a free form.

The cushion holder 9 serves on the one hand to receive the forehead cushion 11 and on the other hand also to receive the head harness 7. The forehead cushion 11 is connected to the cushion holder 9, for example via the cushion receivers 38. In the exemplary embodiment of the forehead support 5, the cushion receivers 38 extend from the holder frame 19, parallel to the indicated z axis, inward into the free space 48 formed by the holder frame 19 and the holder center 47. However, the cushion receivers 38 do not span the whole free space from holder frame 19 to holder center 47, and instead they fill this free space 48 only partially. The cushion receivers 38 are designed, for example, as plates which at one edge are connected to the holder frame 19 or transition into it. The pockets 40 of the forehead cushion 11 can be pulled over these plates, as a result of which the forehead cushion 11 is fixed on the cushion holder 9. In some embodiments, the cushion receivers 38 can also adopt other forms. For example, it is conceivable that the cushion receivers 38 are designed not as plates but as a plurality of rods, in which case the forehead cushion 11 has for example, instead of the pockets 40, several eyelets or tabs which can be pulled over the rods. In some embodiments of the cushion holder 9, in addition to the cushion receivers 38 which protrude inward from the holder frame 19 in the direction of the holder center 47, there are also further cushion receivers which protrude from the holder center 47 into the free space 48. For example, the forehead cushion to be fitted thereto has a corresponding number of pockets which are pulled over the cushion receivers in order to fix the forehead cushion on the cushion holder 9.

The harness receiver 41 forms, with holder frame 19, a gap 36 through which the head harness 7 can be guided and placed around the harness receiver 41. A harness receiver 41 issues in each case from the outer sides of the holder frame 19 (in the z direction). Between the harness receiver 41 and the holder frame 19, a gap 36 forms through which the head harness 7 is guided and then wound around the harness receiver 41. In the embodiment of the forehead support 5 shown in FIGS. 9 and 10, the gap 36 results principally from the fact that the harness receiver 41 protrudes in particular in the x direction (coordinate system of FIG. 10) from the holder frame 19. In some embodiments, the harness receiver 41 can also issue mainly in the z direction from the holder frame 19.

The support arm 6 of the forehead support 5 has, for example, two carriers 28, which are connected in the upper and lower region (according to the y axis) by the connection 23 and the connection 22, respectively. The carriers 28 run parallel to each other, for example. By means of the carriers 28 and the edges of the connections 22 and 23, a free space 37 is formed through which the slide element 10 is plugged onto the support arm 6. The connection 22 here limits how far the slide element 10 can be pushed and in some cases serves also to prevent the slide element 10 from sliding out of the rail 17.

The connection 23 at the lower end of the support arm 6 has a gap 42, for example. The closure tab 21, for example, can be guided through this gap 42 when placed around the connection 23 and pulled over the peg 39.

Figure 10:
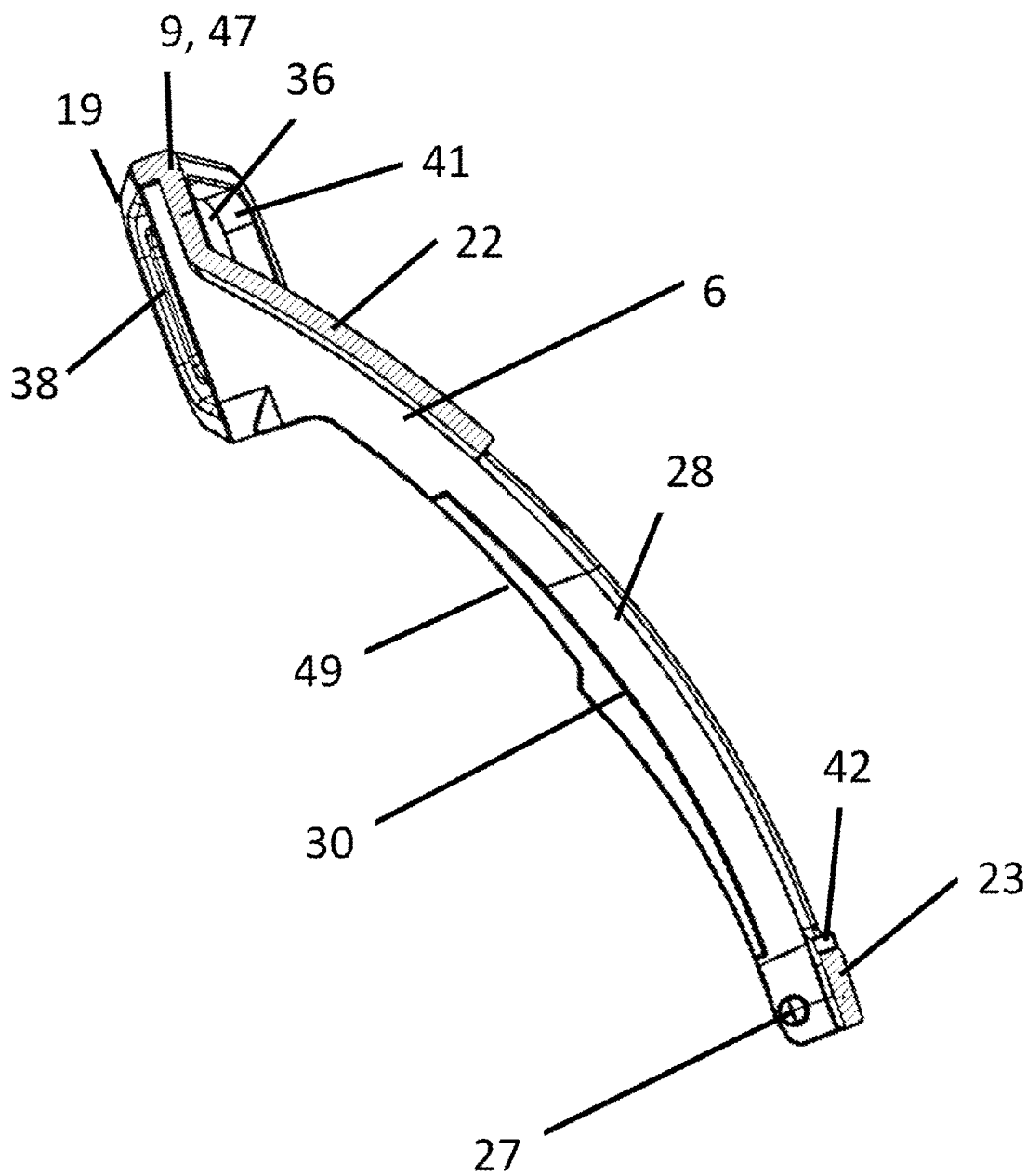
FIG. 10: a longitudinal section through a forehead support

A longitudinal section through the forehead support 5, along the section edge X-X, is shown schematically in FIG. 10. Arranged at one of the ends of the support arm 6 are the pins 27 which are inserted into the connection element 16 in order to produce a rotatable connection between forehead support 5 and mask body 2. The pins 27 at the same time also constitute the pivot axis D about which the forehead support 5 can be pivoted or can rotate. At an edge 49 of the two carriers 28, which are materially connected at one end by the connection 23 and at the other end by the connection 22, respective guide edges 30 are formed which bear on the guide elements 29 of the slide element 10 and/or are clamped by the slide element 10 between slide plate 26 and guide elements 39.

The guide edges 30 have a curved shape, for example, and have a radius R2 which, for example, is equal to the radius R1 of the guide groove 20. For example, the circumference of the circle K2 with radius R2, on which the guide edges extend, does not extend through the pivot axis D. For example, the pivot axis D lies outside the circle K2 with radius R2 on the circumference of which the guide edges 30 extend. In some embodiments, the pivot axis D also lies on the circumference of the circle K2 with radius R2.

In each case, the circle K2 is not congruent with the circle K1; the circles K1 and K2 do not have a common center point. The circles K1 and K2 preferably lie such that they mutually intersect. The intersection points of K1 and K2 can lie in a continuation of the guide groove 20 or of the guide edges 30.

Figure 19:
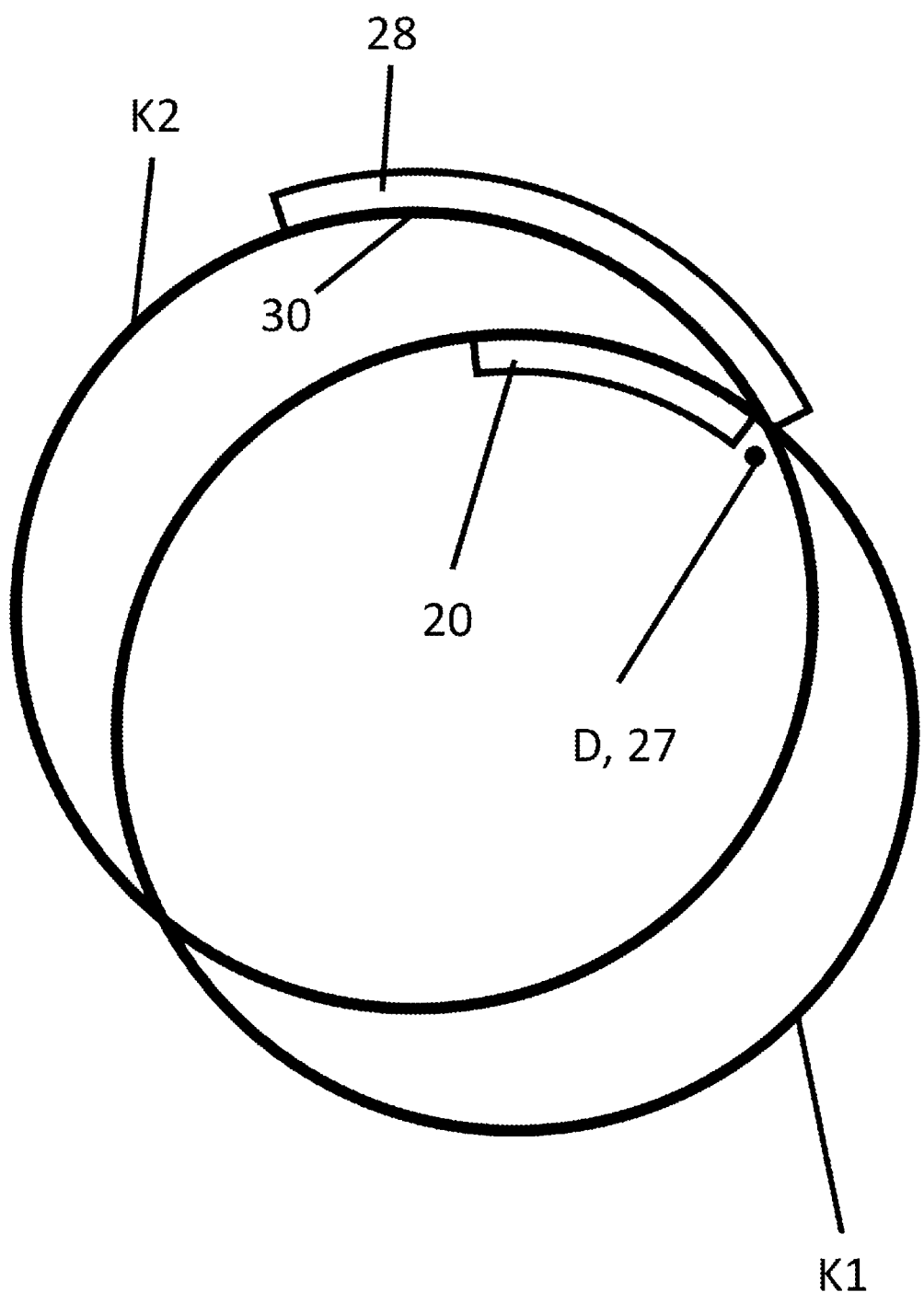
FIG. 19: a schematic representation of the position of the guide groove and of the guide edge with respect to the circles K1 and K2

The pivot axis D can also lie, for example, at an intersection point of the two circles K1 and K2. In some embodiments, the pivot axis lies inside the circle K1 and outside the circle K2. FIG. 19 shows the circles more clearly in relation to pivot axis D, guide groove 20 and guide edge 30.

In some embodiments, the guide edges 30 have a radius R2 which is smaller or greater than the radius R1 of the guide groove 20 of the rail 17. In these embodiments, the degree of pivotability of the forehead support 5 is defined in particular by the radius R2. In some embodiments of the forehead support adjuster, the pivotability of the forehead support is defined by the ratio of the radius R1 to the radius R2, wherein the radius R2 should be smaller or greater than the radius R1. In particular, the ratio between R2 and R1 defines to what extent the forehead support is pivotable. If R1 is greater than R2, the ratio of R2 to R1 is for example in a range R2:R1 of 0.5 to 0.99, preferably in a range of 0.7 to 0.99, more preferably between 0.75 and 0.985. The smaller the ratio of R2 to R1, the greater the angle by which the forehead support 5 pivots upon movement of the slide element 10. A movement of the slide element 10 leads, at a smaller ratio R2:R1, to a greater pivoting angle of the forehead support 5 than for the same movement of the slide element 10 at a greater ratio R2:R1. If R2 is greater than R1, the ratio of R1 to R2 lies for example in a range R1:R2 of 0.5 to 0.99, preferably in a range of 0.7 to 0.99, more preferably between 0.75 and 0.985. If the radii R1 and R2 are different, an intersection point of the respective circles K1 and K2 is not necessary for a pivotability of the forehead support, provided the circles K1 and K2 have no common center point.

For example, the radius R2 measures between 7 and 15 cm, preferably between 9 and 11 cm.

In some embodiments, the guide edge 30 does not have a curved shape that forms the basis of a circle. For example, the guide edge 30 can extend in any desired curving shape, e.g., parabola-shaped, or can be straight. The choice of the course of the guide edge 30 is independent of the shape of the guide groove 20.

At the end of the support arm 6 opposite the pins 27, the connection 22 transitions materially into the holder center 47 of the cushion holder 9. From the holder center 47 there also extends the holder frame 19 from which, among other things, the harness receivers 41 and the cushion receivers 38 start. The harness receivers 41 each form, together with the holder frame 19, a gap 36 through which the head harness 7 can be guided and placed around the harness receiver 41.

Figure 11:
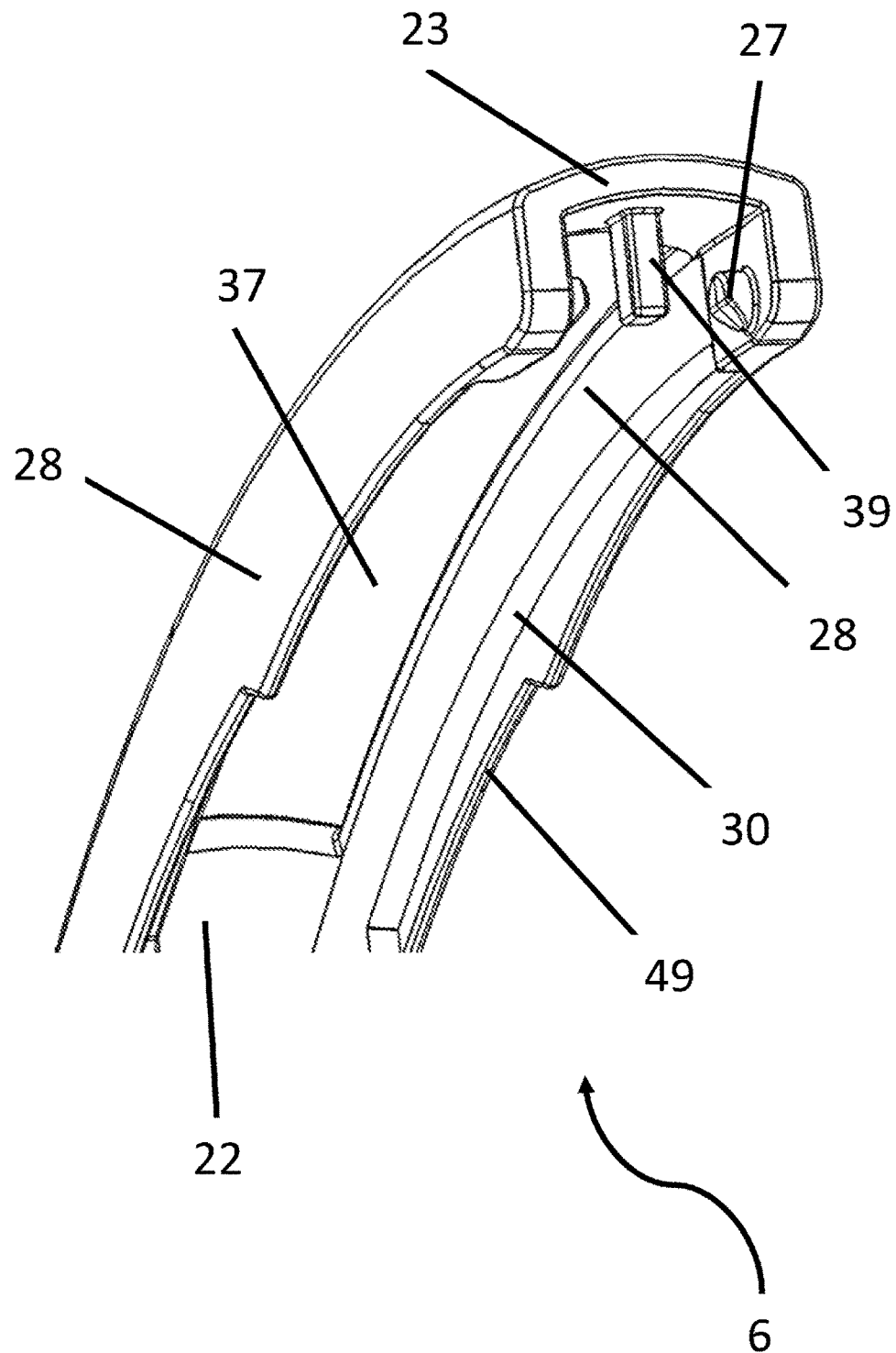
FIG. 11: a detailed view of a support arm in the region of pins for connecting to the connection element

FIG. 11 shows in detail the end of the support arm 6 at which the pins 27 and the peg 39 are arranged. The carriers 28 of the support arm 6 are connected to each other via the connections 22, 23 and delimit, together with the carriers 28, the free space 37 which can receive the slide element 10, by the inner walls 32 of the slide element 10 being plugged through the free space 37. At those edges 49 of the carriers 28 that lie opposite the connections 22, 23, curved (or curve-shaped) guide edges 30 are formed, for example.

These guide edges 30 are arranged internally, for example. In some embodiments, no extra guide edge 30 is formed on the carriers 28, and instead the edges 49 of the carriers 28 themselves serve as guide edges 30.

The connection 23, which interconnects the carriers 28 at the end at which the pins 27 are arranged, has a peg 39 for example. The peg 39 extends for example parallel to the carriers 28 from the connection 29 in the direction of the mask body 2 and is received by the interspace 35 of the connection element 16. The peg 39 can be guided for example through the hole of the closure tab 21 in order to produce a permanent connection between closure piece 15 and mask 1. In some embodiments, the mask body 2 does not have a gas attachment 18, so that the closure piece 15 is also not needed. In these embodiments, the peg 39 can also not be formed on the support arm 6.

The pins 27 are formed at one end of the carriers 28 or of the support arm; the end where the pins 27 are arranged lies opposite the end where the support arm 6 transitions into the cushion holder 9. The pins 27 protrude for example perpendicularly from the carriers 28. For example, the pins 27 are directed inward, i.e. protrude toward each other, but do not touch each other. In some embodiments, the pins 27 are arranged externally on the carriers 28 and are oriented toward the outside, i.e. point away from each other. Instead of the pins, holes can also be formed. If holes are arranged instead of pins 27 at the end of the carriers 28, then the connection element 16 can for example have corresponding pins over which the holes of the support arm 6 are fitted. Alternatively or in addition, both the connection element 16 and the support arm 6 can each have holes. In this case, a rod/a peg is inserted through the holes for the connection. The pivot axis D of the forehead support 5 is defined by the pins 27 of the support arm 6.

An exemplary embodiment of the slide element 10 is shown schematically in FIGS. 12 to 15. The coordinate systems indicated in FIGS. 12 to 15 relate exclusively to FIGS. 12 to 15 and do not correspond exactly to the coordinate systems of the other figures.

Figure 12:
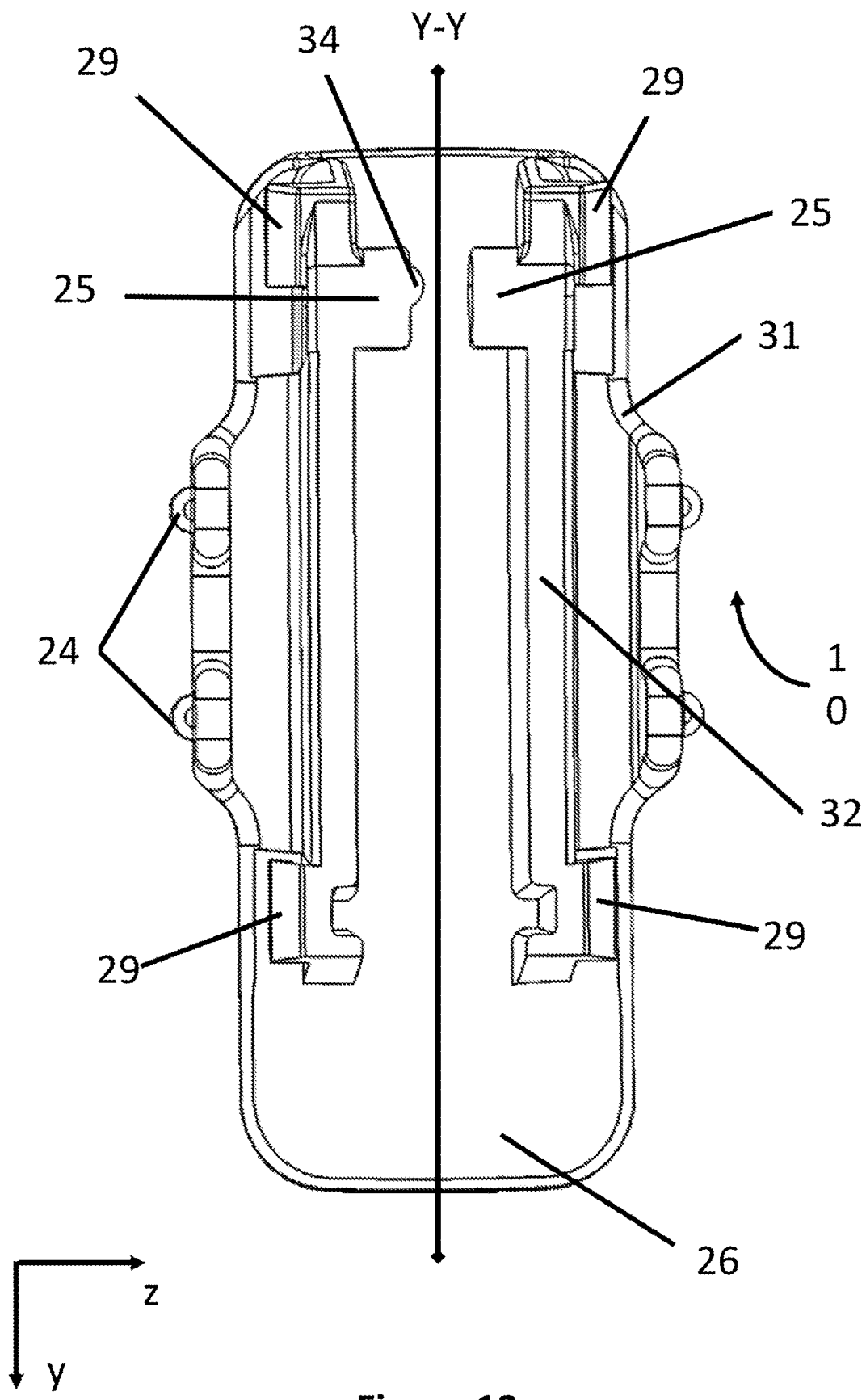
FIG. 12: a bottom view of a slide element

FIG. 12 shows a bottom view of the slide element 10, i.e. the underside of the slide plate 26. On the underside of the slide plate 26, two inner walls 32 are formed which are substantially perpendicular to the slide plate 26 and parallel to each other. The guide elements 29 and the tenons 25 are arranged on the inner walls 32, preferably at the edge of the inner walls 32 lying opposite the slide plate 26. The tenons 25 are arranged for example at one of the corners of the inner walls 32, for example directed inward, i.e. pointing toward each other. A latching lug 34 is additionally formed on at least one of the tenons 25 and can latch into the notches 33 of the rail 17 in order to limit or fix the sliding movement of the slide element 10, such that discrete adjustment steps of the forehead support 5 can be chosen alternately.

In some embodiments, the slide element 10 has only one inner wall, for example with a respective tenon 25 on both sides and guide elements 29 on at least one side. In some embodiments, it is also possible that a third inner wall 32 is arranged in parallel between the two inner walls 32. For example, this inner wall can have additional guide elements 29 and/or tenons 25. Accordingly, further rails 17 or guide grooves 20 and/or also guide edges 30 would also have to be arranged for this purpose.

The guide elements 29 are formed at the same edge of the inner walls 32 where the tenons 25 are arranged. For example, a guide element 29 is arranged at each corner. The guide elements 29 are for example arranged such that they point outward from the inner wall 32, i.e. are oriented away from each other. At least one side, preferably the side pointing to the slide plate 26, is substantially flat, the surface thus shown being in some embodiments curved with a radius R3. In some embodiments, the radius R3 corresponds for example to the radius R2 of the guide edge 30. In some embodiments, the guide elements 29 are configured such that they are adapted to the course of the guide edge 30. In some embodiments, the guide elements 29 are round, such that there is a minimal contact surface between guide element 29 and guide edge 30.

In some embodiments, the guide elements 29 are oriented inward and formed on the inner side of the inner walls 32. Accordingly, in some embodiments, the tenons 25 are arranged on the outer side of the inner walls 32 and are directed outward. In some embodiments, tenons 25 and guide elements 29 are arranged on the same side of the respective inner wall 32. In this case, the guide elements 29 should be offset upward, in the direction of the slide plate 26, and the tenon 25 arranged such that the support arm 6 can be arranged and pivoted above the rail 17.

Instead of two individual guide elements 29 per inner wall 32, in some embodiments a continuous guide element can also be formed per inner wall 32 and extends over the whole or at least most (>50%) of the length (y direction in FIG. 12) of the inner wall 32.

On the outer (z direction) edges of the slide plate 26, the slide plate transitions into the wing elements 31. Grip structures 24 are arranged on the wing elements 31, which in some embodiments transition into at least two subsidiary wings 44, said grip structures 24 allowing a better grip of the slide element 10. The wing elements 31 are substantially perpendicular to the slide plate 26 and extend parallel to the inner walls 32.

Figure 13:
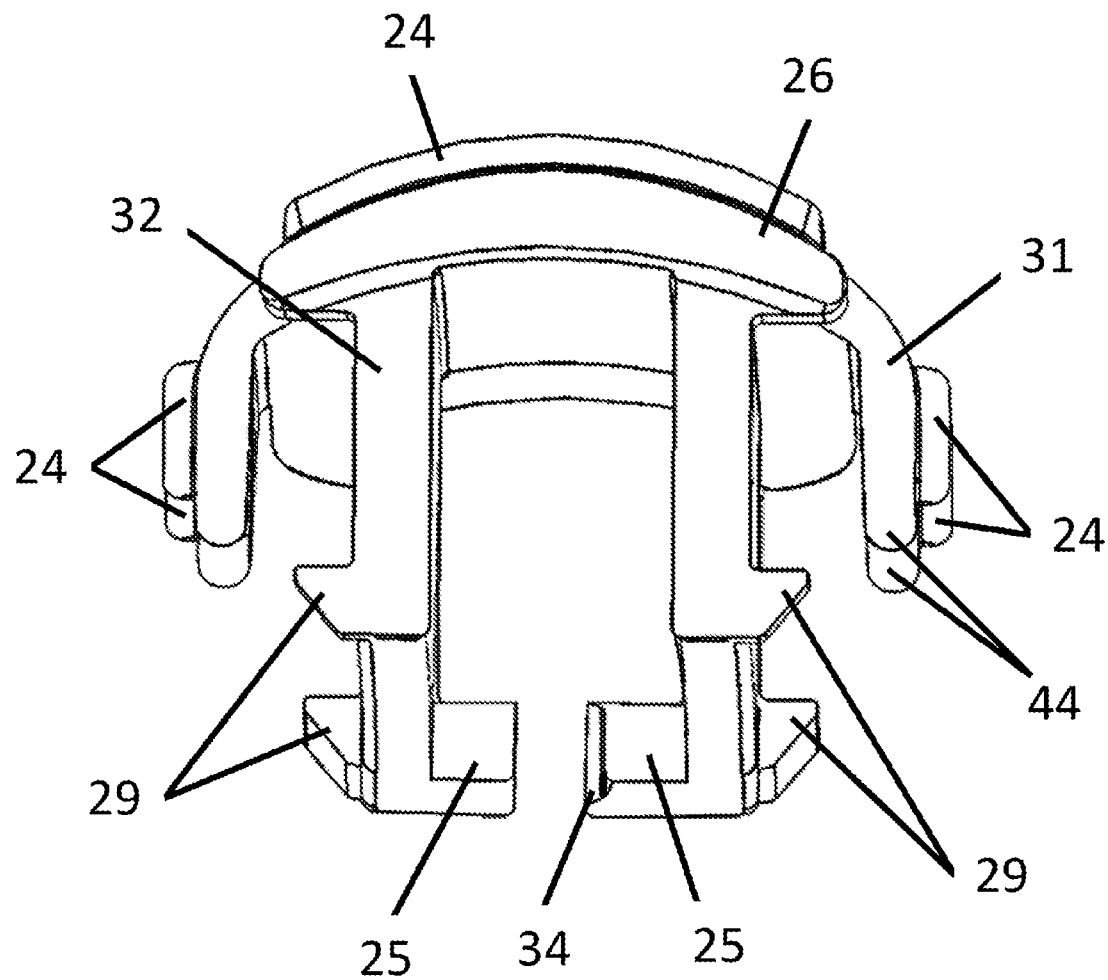
FIG. 13: a rear view of a slide element
Figure 13:
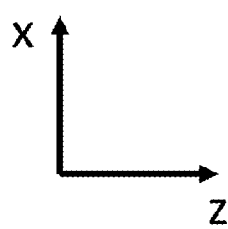

A front view (along the y axis in FIG. 12) of an exemplary embodiment of the slide element 10 is shown in FIG. 13. Grip structures 24 for example, which allow an improved grip of the slide element 10, are arranged on the slide plate 26 and on the sides of the wing elements 31. Two mutually parallel inner walls 32 start out from the slide plate 26. The inner walls 32 are substantially perpendicular to the slide plate 26; in some embodiments the slide plate 26 has a curvature. The wing elements 31, into which the slide plate 26 transitions at the sides, extend parallel to the inner walls 32.

The guide elements 29 are arranged, pointing outward, both in the front region and in the rear region of the inner walls 32. The guide elements 29 protrude perpendicular to the inner walls 32. For example, the guide elements 29 are flat on the side facing the slide plate 26, such that the guide edge 30 can bear thereon. The guide elements 29 are for example angled in a downward direction (x direction), thereby permitting easier insertion into or through the free space 37 of the forehead support 5. The carriers 28 of the support arm 6 are for example clamped movably between slide plate 26 and guide elements 29. A movement of the slide element 10 along the support arm 6 thus remains possible, while an inadvertent release of support arm 6 and slide element 10 is prevented. Moreover, pivoting of the forehead support 5 is not possible without simultaneous rotational movement of the slide element 10; the orientation of the slide element 10 with respect to the support arm 6 always remains the same.

An inwardly directed tenon 25 is arranged in the rear region of each of the inner walls 32 and can be received in the guide groove 20 of the rail 17. The tenons 25 are designed such that they are mounted rotatably and slidably in the guide groove 20. At least one of the tenons 25 has a latching lug 34 which can latch into the notches 33 of the rail 17 in order to fix the setting of the forehead support with respect to an inadvertent adjustment.

Figure 14:
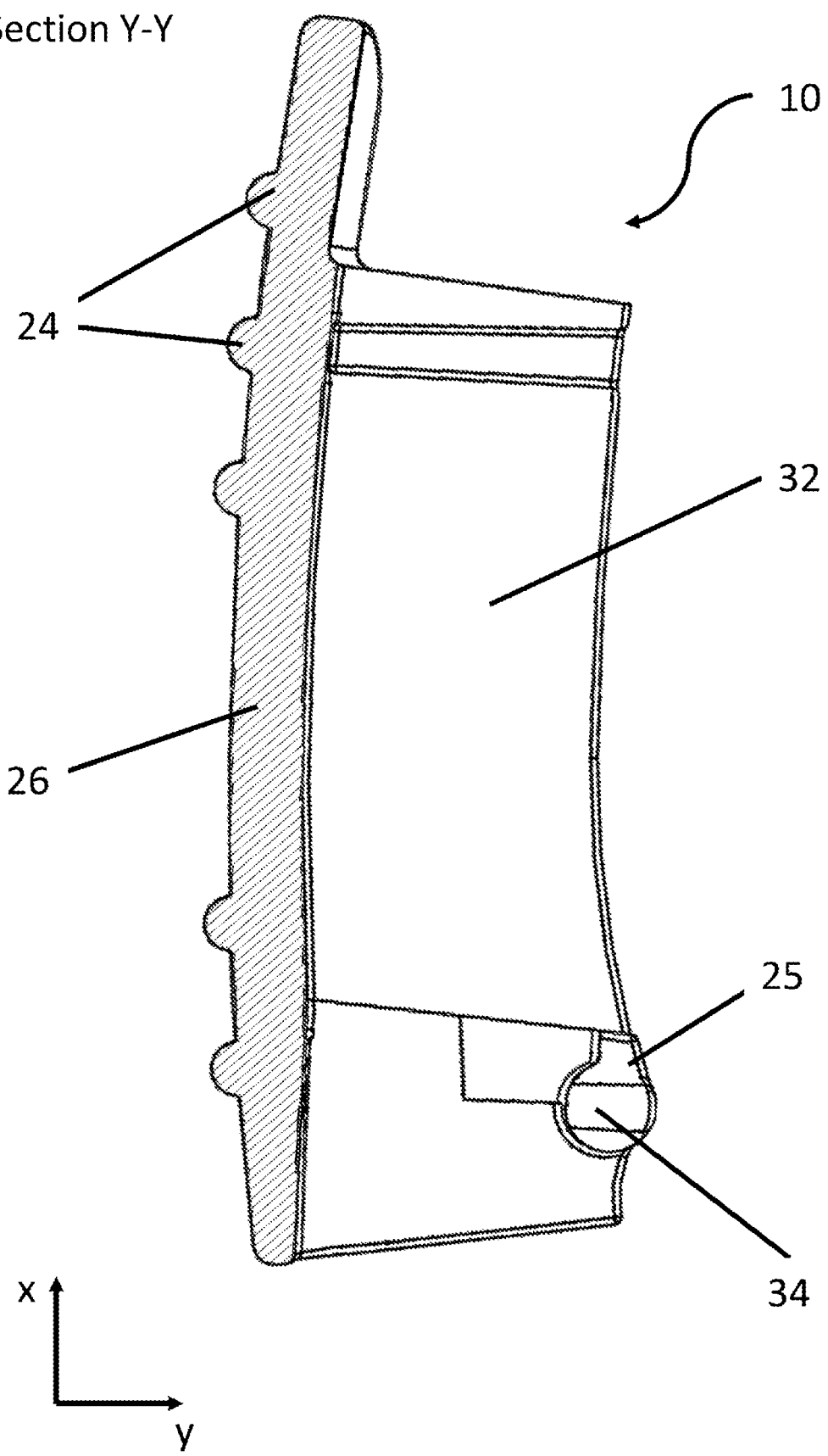
FIG. 14: a longitudinal section through a slide element

FIG. 14 shows a section through an exemplary embodiment of the slide element 10 along the section edge Y-Y (FIG. 12). The slide plate 26 is slightly curved/arcuate, for example, wherein for example an arc is described which corresponds approximately to the radius R2 of the guide edge 30. The radius of the slide plate 26 can deviate slightly (+/−10%) from the radius R2. In some embodiments, the slide plate 26 is also plane/flat. Grip structures 24 are for example arranged on the slide plate 26.

In some embodiments, the slide plate 26 is for example shaped corresponding to the carriers 28. If, for example, the carriers 28 extend in a straight line or in a parabola shape, the slide plate 26 likewise has a straight or parabola-shaped form; however, at least the underside of the slide plate 26, in the regions where the latter bears on the carrier 28, substantially follows the shape of the carrier 28.

The inner wall 32 extends substantially perpendicular to the slide plate 26, on the side of the slide plate 26 lying opposite the grip structures 24. The view shown in FIG. 14 is directed to the inner side of one of the inner walls 32. In one of the corners of the inner wall 32, at the edge lying opposite the slide plate 26, a tenon 25 is formed which is received in the guide groove 20 of the rail 17 in order to achieve rotatable and slidable mounting of the slide element 10 in the rail 17. For example, a latching lug 34 is formed on the tenon 25 and is able to latch into the notches 33 of the guide groove 20 or of the rail 17.

Figure 15:
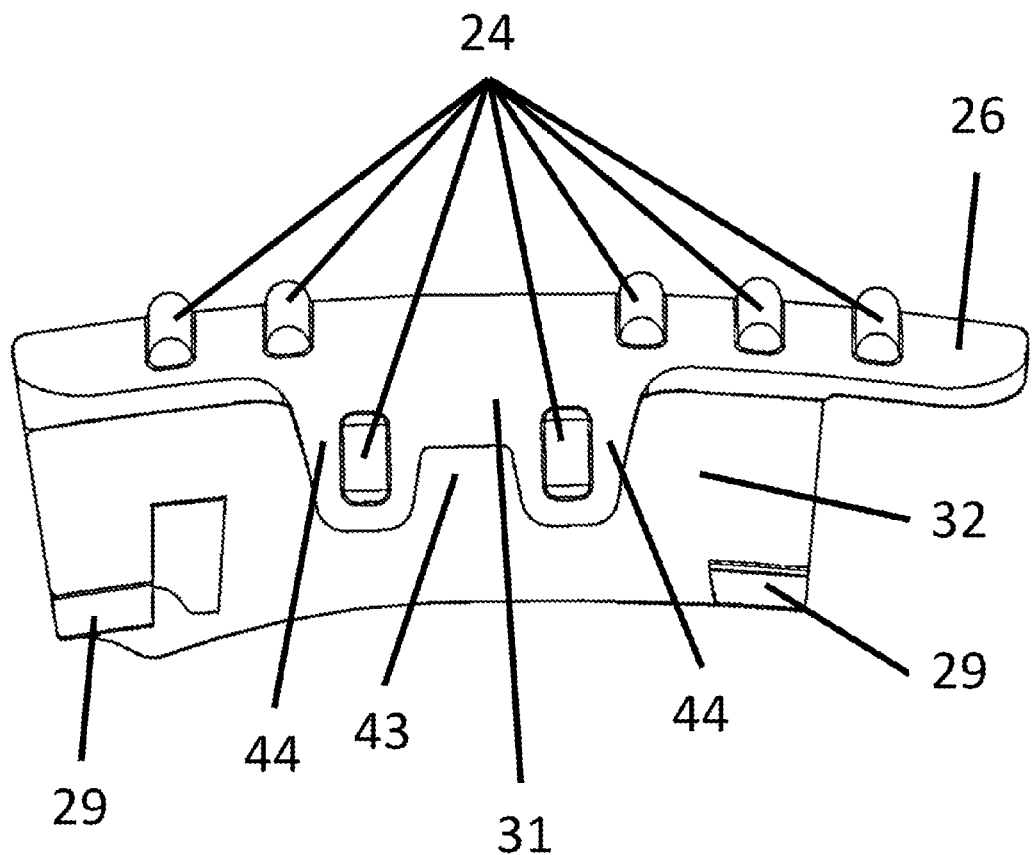
FIG. 15: a side view of a slide element
Figure 15:
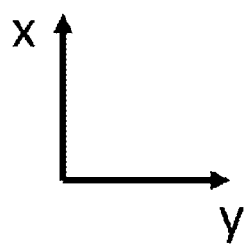

FIG. 15 shows a side view of an exemplary embodiment of the slide element 10. The slide plate 26 transitions for example into the wing 31 which runs parallel to the inner wall 32. The wing 31 has, for example, two subsidiary wings 44, on each of which a grip structure 24 is arranged. An interspace 43 is located between the subsidiary wings 44. In some embodiments, discrete markings (for example a numbering and/or value indications, e.g. pivoting angle) for the pivoting positions and/or for marking the pivoting position are arranged, for example printed, on the outer side of the support arm 6. A pivoting position can for example be characterized in that the slide element 10 in the corresponding position is able to latch with the latching lug 34 in a notch 33. These markings are for example arranged such that the marking corresponding to the pivoting position can in each case be seen in the interspace 43 between the subsidiary wings 43.

The two guide elements 29 shown in FIG. 15 are for example arranged at a slight angle to each other. The guide elements 29 angled relative to each other correspond substantially to the arc-shaped/curved profile of the guide edge 30. In some embodiments, the guide elements 29 themselves are curved, such that the described arc has a radius R3 which substantially corresponds to the radius R2 of the guide edge 30.

The guide elements 29 are for example formed with an elongate extent (in y direction of FIG. 15). In some embodiments, the guide elements 29 can also have a substantially round shape in a plan view (along the viewing axis in FIG. 15).

Figure 16:
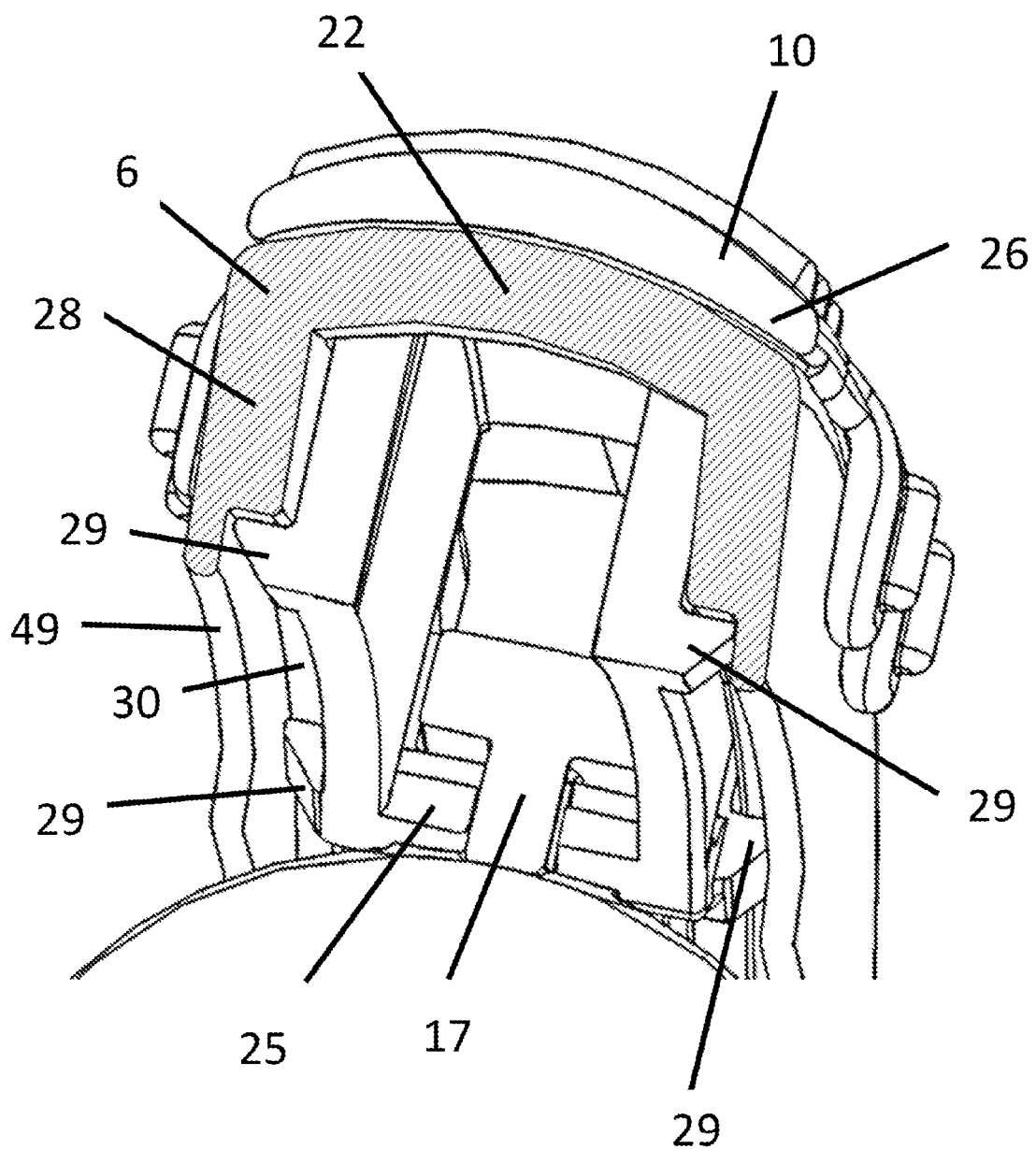
FIG. 16: a cross section through a support arm

FIG. 16 shows a section through an exemplary embodiment of the support arm 6 in an exemplary arrangement with a rail 17 on the mask body 2 and with an inserted slide element 10. The section plane through the support arm 6 is set directly after the start of the connection 22 in the attachment to the free space 37. In the view shown, the slide element 10 is for example located with the latching lug 34 on one of the tenons 25 in the last notch of the rail 17, that is to say in the position farthest from the connection element 16. A further movement of the slide element 10 away from the connection element 16 is prevented by the connection 22, on which the slide element 10 abuts with the inner walls 32. In this setting, the forehead support 5 lies closest to the mask body 2. If the slide element 10 is pushed in the direction of the connection element 16, the support arm 6 is pivoted about the pivot axis D, which for example is defined by the pins 27 in the connection element 16.

The tenons 25 of the slide element 10 are rotatably and slidably mounted in the guide groove 20 of the rail 17 and can thus be moved along the rail 17 and rotated in the process. The carriers 28 of the support arm 6 bear for example with the guide edge 30 on the guide elements 29 of the slide element 10 or are clamped between the slide plate 26 and the guide elements 29. Depending on the direction of movement of the slide element 10, either the slide plate 26 presses from above on the carriers 28 or the guide elements 29 press from below on the guide edge 30 in order to effect a pivoting movement of the forehead support 5 about the pivot axis D. The wing elements 31 of the slide element 10 are arranged on the slide element 10 such that they are arranged externally (in the z direction) on the sides of the carriers 28. The inner walls 32 of the slide element 10 are located for example on the side of the carriers 28 opposite the wing elements 31.

If the slide element 10 is pushed in the direction of the connection element 16, the slide element 10 is guided along the guide groove 20 of the rail 17. Since the circles of the guide edge 30 of the support arm 6 and of the guide groove 20 do not have a common center point or the contours of the guide groove 20 and of the guide edge 30 do not run parallel, the guide elements 29 come into contact with the carriers 28 or the guide edge 30 during the movement. Since the support arm 6 is mounted pivotably in the connection element 16, a pivoting of the support arm 6 can take place, as a result of which it yields to the pressure of the guide elements 29 of the slide element 10. The carriers 28 in turn exert a pressure on the slide plate 26 through the pivoting movement of the forehead support 5. In order to yield to this pressure, the whole slide element 10 rotates in the guide groove 20. In the sliding movement of the slide element 10 in the direction of the connection element 16, the slide element 10 and the forehead support 5 thus pivot or rotate simultaneously. The axis of pivoting or axis of rotation of the slide element 10 runs through the two tenons 25.

Figure 17:
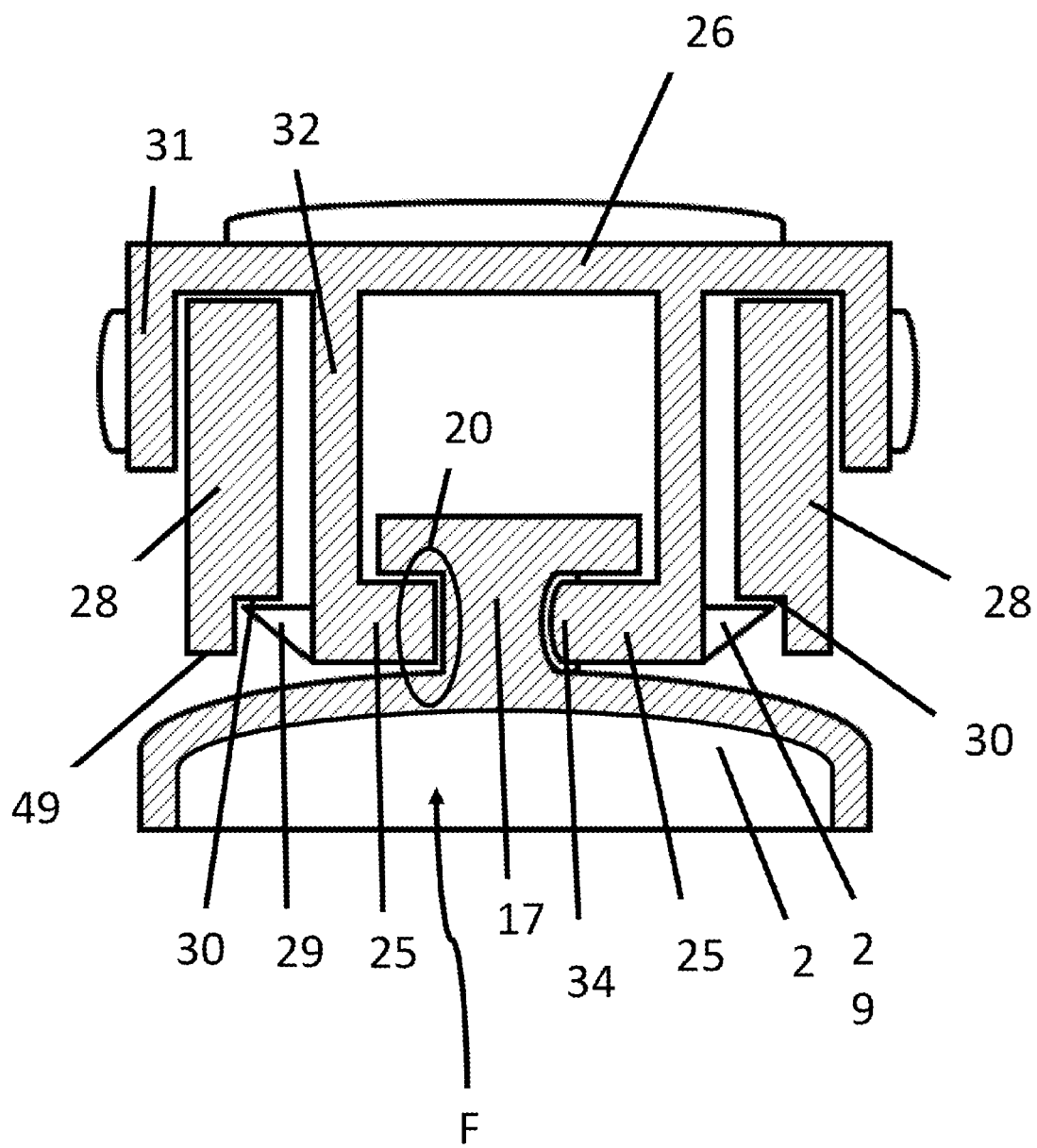
FIG. 17: a cross section through rail/support arm/slide element

FIG. 17 shows a section through an exemplary embodiment of the forehead support adjuster consisting of slide element 10, forehead support 5 and rail 17. The carriers 28 are clamped between slide plate 26 and guide elements 29, the guide edge 30 bearing on the guide elements 29. In some embodiments, no special guide edge 30 is formed on the carriers 28, and therefore the lower edge of the carrier 28 itself constitutes the guide edge 30.

The tenons 25 of the slide element 10 run in the guide groove 20 of the rail 17. On one of the tenons 25, a latching lug 24 for example is arranged which is able to latch in the notches 33 of the rail 17 and thereby prevents an inadvertent sliding movement of the slide element 10 and fixes the forehead support 5 in a pivoting position. At the sides of the carriers 28, the wing elements 31 and the inner walls 32 extend perpendicularly from the slide plate 26.

For example, the tenons 25 and the guide elements 29 are arranged at the same height (x direction in FIG. 17) on the inner walls 32 of the slide element 10. In some embodiments, the tenons 25 and the guide elements 29 can also be arranged at different heights. In some embodiments, the arrangement on the outer side (guide elements 29) and inner side (tenons 25) of the inner walls 32 may also be different. In some embodiments, the forehead support adjuster is for example constructed such that the carriers 28 run with the guide edge 30 centrally, above the rail 17. In this case, guide elements 29 and tenons 25 would both be arranged on the inner sides of the inner walls 32. The tenons 25 are in each case to be arranged on that side of the inner walls 32 on which the rail 17 with the guide groove 20 runs. The guide elements 29 are in each case to be arranged on the side on which the guide edge 30 runs.

The rail 17 is for example connected materially to the mask body 2. For example, mask body 2 and rail 17 are produced in one piece. In some embodiments, however, the rail 17 can also be produced as an extra and placed onto the mask body 2 and connected to the mask body 2 by plugging, clamping, adhesive bonding and/or screwing or by similar connection methods.

The illustrative pivoting range of the forehead support 5 is shown in FIGS. 18A and 18B. In FIG. 18A, the slide element 10 is in the latching position which lies closest to the connection element 16 and thus to the pivot axis D. The latching lug 34 is thus latched in the notch 33 which lies closest to the connection element. In this position, a plane A can for example be defined between cushion holder 9 and forehead cushion 11, said plane A being defined substantially by the surface of the cushion holder 9. This plane A can be shifted in parallel so that the pivot axis D lies on the plane A.

In FIG. 18B, the slide element 10 is located in the latching position which lies farthest away from the connection element 16 and therefore the pivot axis D. Considering here the plane B, which for example can be defined on the basis of the surface of the cushion holder 9, it is rotated relative to the plane A by the angle C. The angle C constitutes for example the maximum pivoting angle of the forehead support 5 about the pivot axis D. For example, the maximum pivoting angle C of the forehead support 5 lies in a range from 10° to 40°, preferably between 15° and 25°.

The maximum pivoting angle C here indicates the change of the angle that arises between the respective first and last pivoting positions. For example, the pivoting angle at which the slide element 10 sits in the latching position closest to the connection elements 16 can be defined as 0°. In the latching position farthest from the connection element 16, the pivoting angle then assumes the value of the maximum pivoting angle C.

The maximum pivoting angle C depends on a number of factors. In particular, the distance by which the slide element 10 can be moved influences the maximum pivoting angle. The longer this distance is chosen to be, the greater the pivoting angle C. The distance by which the slide element 10 can be moved in the guide groove 20 is for example between 2 cm and 10 cm, preferably between 2.5 cm and 5 cm, more preferably between 2.5 and 4 cm.

Moreover, the maximum pivoting angle is defined by the ratio of the radius R2 of the guide edge 30 to the radius R1 of the guide groove 20. For example, the maximum pivoting angle C increases, with a constant distance for the slide element 10, when the ratio R2:R1 decreases. If the distance by which the slide element 10 can be moved is lengthened, the maximum pivoting angle C increases at constant ratio R2:R1.

During the pivoting of the forehead support 5 about the pivot axis D, the positioning of the cushion holder 9 changes and thus also the positioning of the forehead cushion 11 relative to the mask body 2. The orientation of the forehead cushion 11 also changes by the angle C. As has been described for FIGS. 18A and 18B, the forehead cushion moves counter to the x direction and counter to the y direction during the pivoting of the forehead support 5. From FIG. 18A to FIG. 18B, the forehead support 5 is basically guided closer to the mask body 2.

If the slide element 10 is moved along the rail 17 in the direction of the cushion holder 9, for example from the position in FIG. 18A to the position in FIG. 18B, the support arm 6 approaches the mask body 2, until the maximum pivoting position is reached.

Assuming that the mask is resting on a face, and the forehead support 5 is fixed with a head harness on the forehead of the user, an adjustment of the forehead support 5 would effect a change of the positioning of the mask body 2. For example, by a movement of the slide element 10 to the latching position farthest from the connection element 16, the upper region of the mask body 2 is pressed away from the user's face.

An example of the relative position of the circles K1 and K2, with the guide groove 20 and guide edge 30 extending on the respective circumference, is shown schematically in FIG. 19. The position shown is for example only valid for one pivoting position. The circles K1 and K2 have radii R1 and R2, which are of the same magnitude for example. The center points of the circles K1 and K2 are offset relative to each other, such that the circles intersect. The guide groove 20 runs along a partial segment of the circumference of the circle K1. The guide edge 30 runs along a partial segment of the circumference of the circle K2. For example, guide edge 30 and also guide groove 20 have an end in the region of the point of intersection of the circles K1 and K2. In the exemplary embodiment shown, the pivot axis D, which is defined for example by the pins 27, is located inside the circles K1 and K2. During the movement of the slide element 10, the circle K2 turns about the pivot axis D while the circle K1 remains fixed. In this way, the guide edge 30 pivots relative to the guide groove 20 about the pivot axis D. In some embodiments, the pivot axis D can be arranged freely. Thus, an arrangement outside K1 but inside K2, an arrangement outside both K1 and K2, and also an arrangement on the circumference of K1 and/or K2 are possible. During the pivoting of the carrier 28 about the pivot axis D, the position of the circles K1 and K2 relative to each other also changes at the same time. By virtue of the fact that the circles K1 and K2 come into a congruent position or the circles run parallel to each other, it is for example possible to prevent a situation where the distance J between the guide elements 29 and the tenons 25 does not correspond to the distance K between the top edge 51 of the guide groove 20 and the guide edge 30, when the guide groove 20 and the guide edge 30 are set parallel to each other by a pivoting about the pivot axis D.

Whether the pivot axis D is inside or outside the circle K2 which is rotatable about the pivot axis D depends primarily on the current pivoting position. However, in connection with the maximum pivoting angle C, it is possible to ensure that the pivot axis D always lies outside or inside the circle K2. It is thus also possible to ensure, for example, that during a pivoting movement the position of the pivot axis D relative to the circle K2 alternates from inside to outside and vice versa.

Also in the case of a straight or parabola-shaped course of the guide groove 20 and of the guide edge 30, the distance J between the guide elements 29 and the tenons 25 should not correspond to the distance K between the top edge 51 of the guide groove 20 and of the guide edge 30 in a parallel setting, since otherwise no pivoting movement can be achieved through the sliding of the slide element 10. The distance J between the guide elements 29 and the tenons 25 is preferably greater than the distance K between the top edge 51 of the guide groove 20 and of the guide edge 30, when these extend parallel to each other through a pivoting position.

Figure 20A:
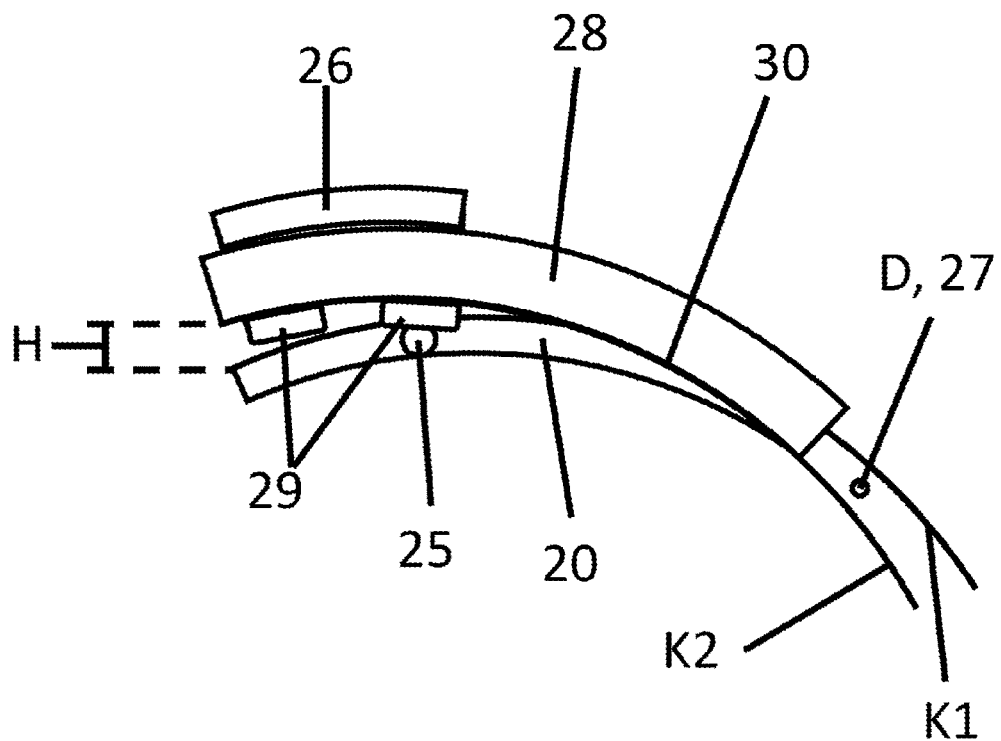
FIGS. 20A and 20B: a schematic representation of the function of the forehead support adjuster
Figure 20B:
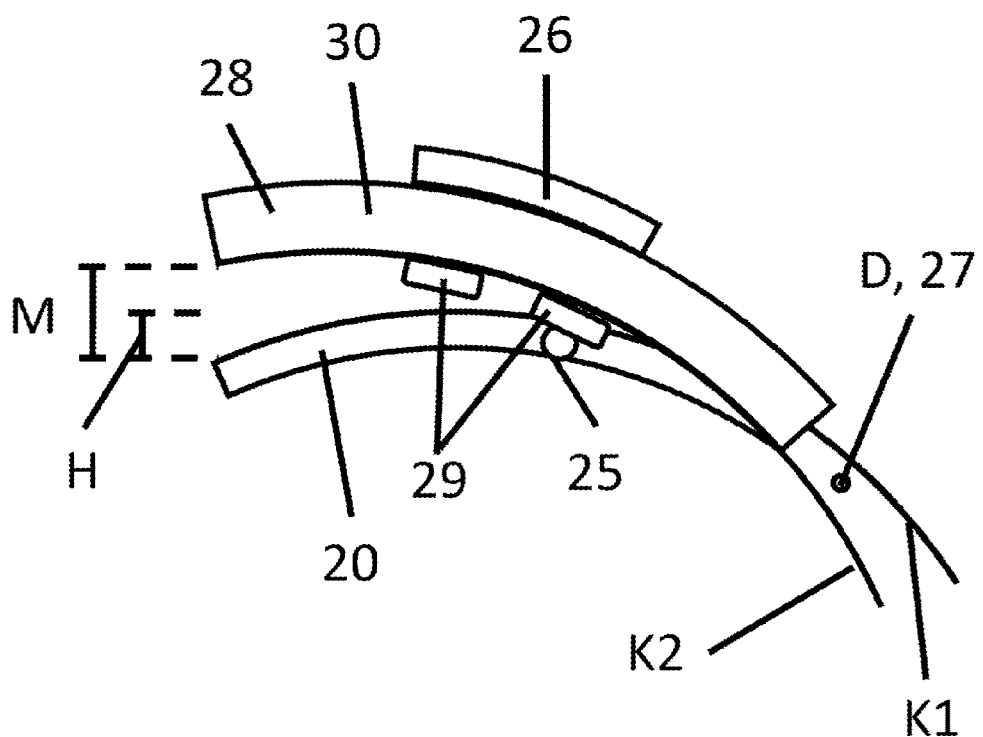

The function of an exemplary embodiment of the forehead support adjuster is shown schematically in FIG. 20, in which only the tenons 25, the slide plate 26 and the guide elements 29 of the slide element 10 are shown. For example, an embodiment is shown in which guide groove 20 and also guide edge 30 and carrier 28 have a curved shape and follow a circumference of a circle. The radius R2 is for example equal to the radius R1, the circles K1 and K2 intersect for example, and the pivot axis D lies for example outside circle K2 and inside circle K1. The profile of the circles K1 and K2 is indicated for example by the continuations designated K1 and K2. The slide element 10 comprises, among other things. the slide plate 26, the tenons 25 and the guide elements 29, which are arranged at a fixed distance to one another. This is achieved, for example, by the slide element 10 being produced in one piece.

If the slide element 10 is moved in the direction of the pivot axis D, which is defined for example by the position of the pins 27, the tenons 25 are guided along the guide groove 20. The guide elements 29 press on the guide edges 30 of the carriers 28 (part of the support arm 6). In this way, the support arm 6 is pivoted about the pivot axis D. The carrier 28 is clamped between the slide plate 26 and the guide elements 29, the arrangement of the slide plate 26 and of the guide elements 29 being adapted to the contour of the carriers 28. In order to further follow this contour during the pivoting of the carriers 28, the guide elements 29 and the slide plate 26 move along the carrier. In the process, the slide element 10 at the same time rotates about the tenons 25.

If the slide element 10 is moved away from the pivot axis D, the slide plate 26 for example presses on the carriers 28. As a result of this, a rotational movement of the slide element 10 about the tenons 25 takes place.

The slide element 10 is configured to follow the profile of the circle K1, i.e. of the guide groove 20, and also the profile of the circle K2, i.e. of the guide edge 30, and/or the carrier 28. The two circles are not congruent, such that, for example during a movement of the slide element 10 along the guide groove 20, a change of the orientation of the slide element 10 by a rotation about the tenons 25 is necessary at the same time, so that the slide element 10 is able to follow both profiles, of K1 and K2.

In some embodiments, a movement of the slide element 10, i.e. a movement with simultaneous rotation about the tenons 25, can for example also be achieved when the forehead support 5 is pivoted about the pivot axis D. Depending on the direction of pivoting, the carrier 28 applies pressure to the slide plate 26 or the guide elements 29, which then seek to follow the contour of the carriers 28 or of the guide edge 30.

In the position A in FIG. 20, the guide edge 30 has at one end a distance H from the guide groove 20. If the slide element 10 is pushed in the direction of the pivot axis D (position B in FIG. 20), the support arm 20 pivots, as a result of which the distance of the guide edge 30 from the guide groove 20 increases to the distance M. By the movement of the slide element 10 in the direction of the pivot axis D, the distance between carrier 28 and guide groove 20 increases, i.e. also from the mask body 2.

Figure 21A:
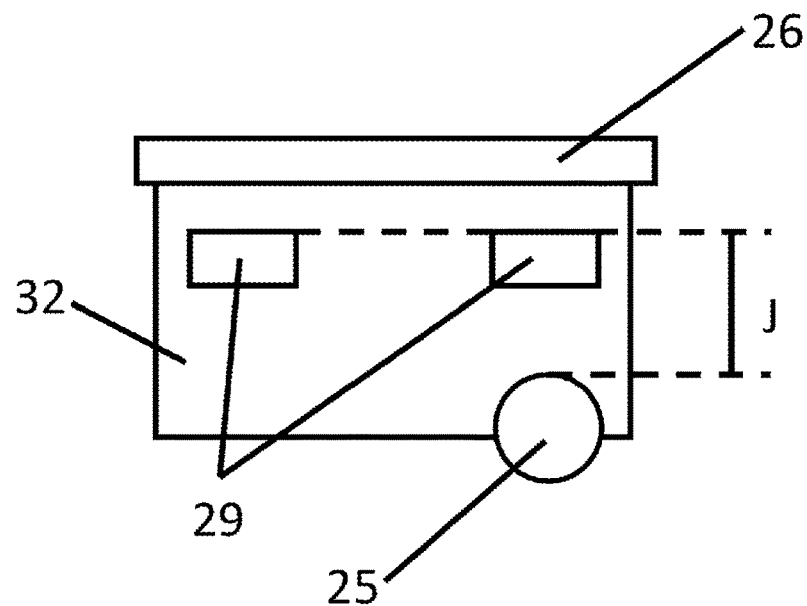
FIGS. 21A and 21B: a schematic representation of the distances between tenons and guide elements

FIG. 21A shows a greatly simplified, schematic view of an exemplary embodiment of the slide element 10. Here, reference is made in particular to the distance J between the top edge (in x direction) of the guide elements 29, which are arranged at the same distance J from the tenon 25 and are straight, and the uppermost point of the tenon 25. The distance J is preferably not equal to the distance K between the top edge 51 of the guide groove and the guide edge 30 when, by pivoting, they are brought to a position in which guide groove 20 and guide edge 30 run parallel to each other or, in the case of curved shapes of identical radius, are congruent.

Figure 21B:
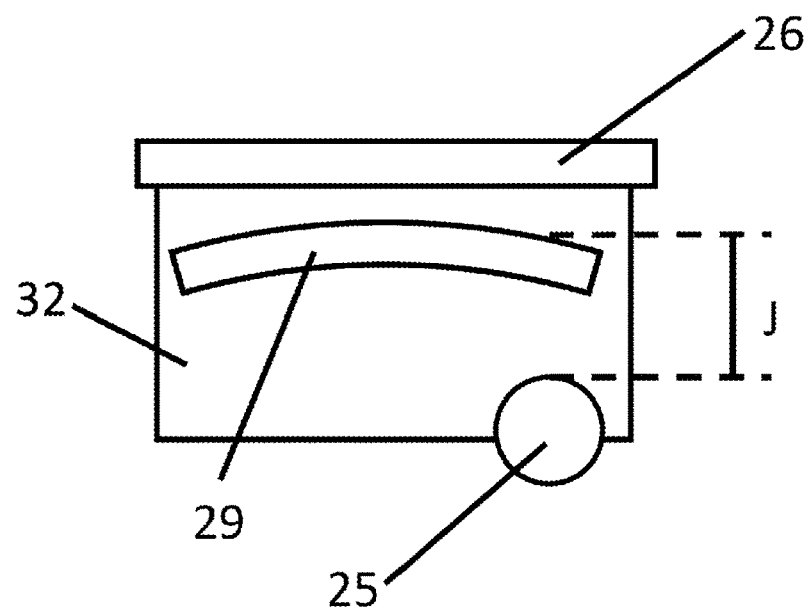
Figure 21B:
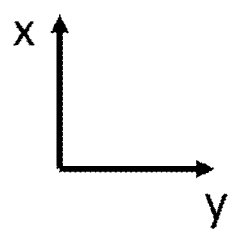

FIG. 21B shows an individual guide element 29 which for example is curved and is designed with the radius R3, where the radius R3 corresponds for example to the radius R2 of the guide edge 30. In such an embodiment, the distance J is between the highest point in the x direction of the tenon 25 and the point, lying exactly opposite in the x direction, on the guide element 29.

Figure 22A:
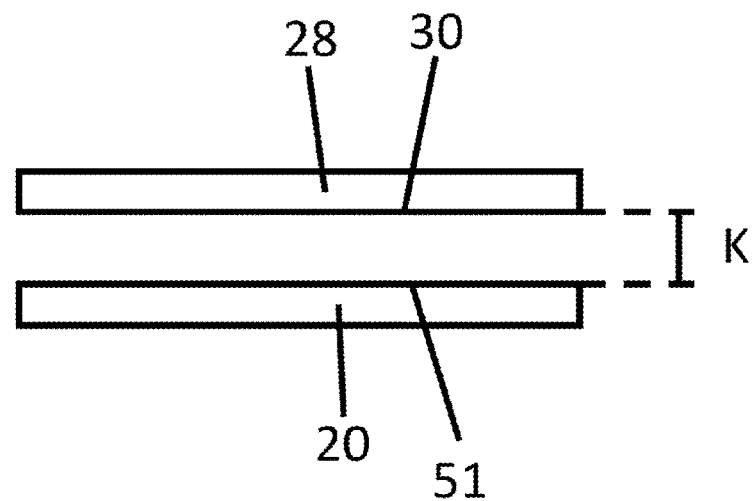
FIGS. 22A and 22B: a schematic representation of the distances between guide groove and guide edge The coordinate systems shown in some of the figures serve primarily to illustrate the orientation of the view; unless otherwise stated, the x, y and z axes describe the same direction in each case, i.e., the direction designated by the x axis in one figure corresponds to the direction of the x axis of another figure.
Figure 22B:
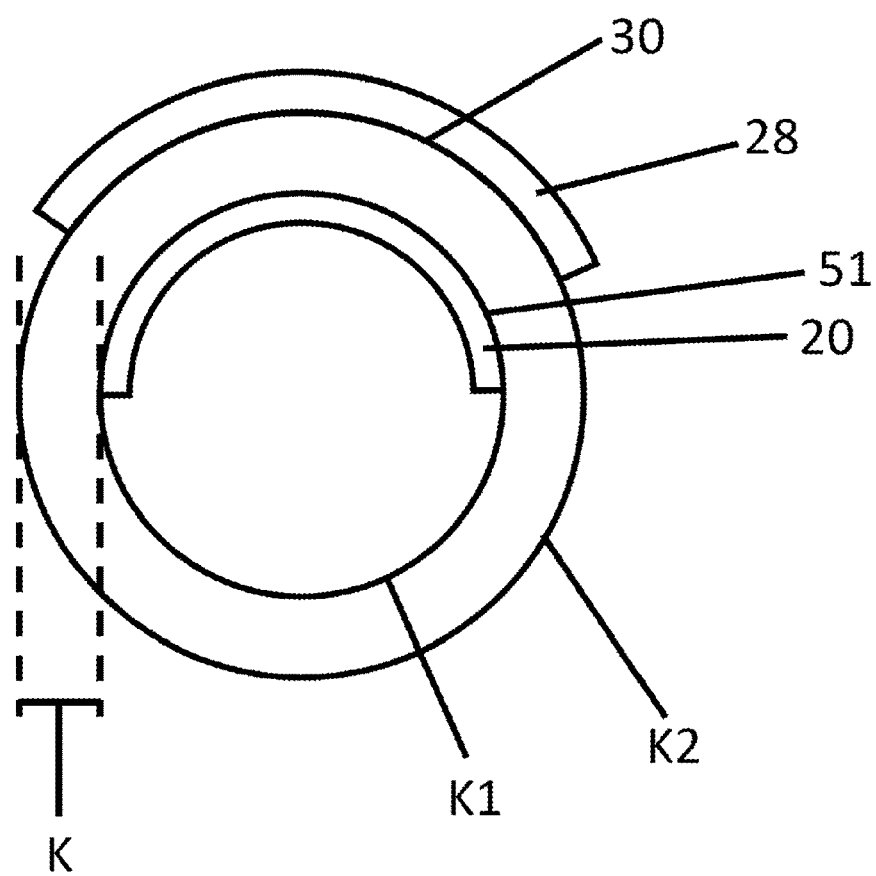

FIG. 22A and FIG. 22B show, as examples, two cases in which the guide groove 20 and the guide edge 30 are brought into a parallel course by pivoting about the pivot axis (not shown; the exact position of the pivot axis is unimportant here). In FIG. 21A, guide groove 20 and guide edge 30 are straight and run parallel to each other at a distance K. The distance J (cf. FIG. 21A) between guide elements 29 and tenons 25 should preferably be greater than the distance K.

In FIG. 22B, the guide groove 20 and the guide edge 30 follow a curved course along the circles K1 and K2, respectively, where the circle K1 has a smaller radius than the circle K2. The circles K1 and K2 extend parallel to each other, and the tangents have the distance K from each other at each position. If the distance between the guide elements 29 and tenons 25 were equal to the distance K, the slide element 10 could be moved along the guide groove 20 without there being a pivoting movement of the carrier 28 about the pivot axis D, since the guide elements 29 could also follow the guide edge 30 without resistance.

LIST OF REFERENCE SIGNS 1 mask
2 mask body
3 face cushion
4 hose attachment
5 forehead support
6 support arm
7 head harness
8 harness clip
9 cushion holder
10 slide element
11 forehead cushion
12 cushion attachment
13 clip holder
14 attachment
15 closure piece
16 connection element
17 rail
18 gas attachment
19 holder frame
20 guide groove
21 closure tab
22 connection
23 connection
24 grip rib
25 tenon
26 slide plate 27 pin
28 carrier
29 guide element
30 guide edge
31 wing element
32 inner wall
33 notch
34 latching lug
35 interspace
36 gap
37 free space
38 cushion receiver
39 peg
40 pocket
41 harness receiver
42 gap
43 interspace
44 subsidiary wing
45 attachment lock
46 wall
47 holder center
48 free space
49 edge
50 guide groove
51 top edge
A plane
B plane
C angle
D pivot axis
E outer side
F inner side
G plane of symmetry
H distance
J distance
K distance
M distance
R1 radius (guide groove 20)
R2 radius (guide edge 30)
R3 radius (guide elements 29)
K1 circle (guide groove 20)
K2 circle (guide edge 30)

What is claimed is:

1. A forehead support adjuster for a mask, wherein the forehead support adjuster comprises at least
   a. a forehead support having a support arm and cushion holder,
   b. a connection element,
   c. a rail with at least one guide groove,
   d. a slide element,
the slide element comprising at least one slide plate, at least one tenon and at least one guide element, the at least one tenon being mounted rotatably and slidably in the at least one guide groove of the rail, and the slide element being movably connected to the support arm, and wherein the forehead support adjuster is configured such that a movement of the slide element along the rail results in a pivoting of the forehead support about at least one pivot axis D, and wherein
   (i) at least two notches are arranged in the rail, and a latching lug is arranged on the at least one tenon, configured so that the latching lug can latch into the at least two notches and thereby fix a pivoting position; and/or
   (ii) the support arm comprises at least two carriers, which are arranged parallel to each other and are connected to each other via connections which, together with the at least two carriers, form a free space through which the slide element is at least partially plugged; and/or
   (iii) the support arm transitions at one end into the cushion holder, at an end of the support arm lying opposite the end with the cushion holder a peg being arranged on a connection, via which peg a closure piece is connected captively to the mask, and the cushion holder comprising a holder frame which, together with a holder center, forms a free space into which at least one cushion receiver protrudes from at least one side of the holder frame, in a direction of the holder center, and serves to receive a forehead cushion.

2. The forehead support adjuster of claim 1, wherein at least one inner wall is arranged on the slide plate, the at least one tenon and the at least one guide element being arranged on the inner wall.

3. The forehead support adjuster of claim 1, wherein at least (i) applies.

4. The forehead support adjuster of claim 1, wherein the support arm comprises at least one carrier which is rotatably connected to the connection element via at least one pin.

5. The forehead support adjuster of claim 4, wherein the slide plate has, at two mutually opposite sides, respective wings which are substantially perpendicular to the slide plate and comprise at least in each case two sub-wings, an interspace being present between the respective sub-wings, and wherein discrete markings for marking a pivoting position are arranged on at least one side of the at least one carrier, wherein the discrete markings are arranged such that at least one marking can be seen in an interspace between the sub-wings when a latching lug fixes a corresponding pivoting position.

6. The forehead support adjuster of claim 1, wherein the rail and the connection element are integrated in a mask body.

7. The forehead support adjuster of claim 1, wherein at least (ii) applies.

8. The forehead support adjuster of claim 7, wherein the carriers of the support arm comprise at least one guide edge, along which the guide elements are guided.

9. The forehead support adjuster of claim 1, wherein at least two inner walls are arranged on the slide plate and are arranged substantially perpendicular to the slide plate, and wherein tenons and guide elements are arranged at edges that lie opposite the slide plate.

10. The forehead support adjuster of claim 1, wherein the guide elements and tenons are arranged at a distance J from each other, and a guide edge and a top edge of the guide groove are at a distance K from each other when the guide edge and the guide groove extend parallel to each other, the distance J being not equal to the distance K and not changing during a movement of the slide element.

11. The forehead support adjuster of claim 10, wherein the guide edge has a curved or straight configuration, a curved guide edge having a radius R2, a radius R1 of the at least guide groove in a curved configuration being not equal to the radius R2, and a ratio R2:R1 or R1:R2 ranging from 0.5 to 0.99.

12. The forehead support adjuster of claim 11, wherein the radii R1 and R2 range from 7 cm to 15 cm.

13. The forehead support adjuster of claim 1, wherein the at least one guide groove has a curved or straight configuration, a curved guide groove having a radius R1.

14. The forehead support adjuster of claim 1, wherein the forehead support can be pivoted by a maximum pivoting angle C of from 10° to 40°.

15. The forehead support adjuster of claim 1, wherein a top edge of the at least one guide groove lies on a circle K1 with a radius R1, and a guide edge lies on a circle K2 with a radius R2.

16. The forehead support adjuster of claim 15, wherein the pivot axis D always has the same relative position, i.e., lying inside or outside, with respect to the circles K1 and K2 when a maximum pivoting angle C is not exceeded.

17. The forehead support adjuster of claim 16, wherein the pivot axis D always lies outside the circle K2 and always inside the circle K1.

18. The forehead support adjuster of claim 1, wherein a sliding of the slide element along the rail in a direction of the cushion holder causes the support arm to approach a mask body.

19. The forehead support adjuster of claim 1, wherein at least (iii) applies.

20. A mask, wherein the mask comprises the forehead support adjuster of claim 1 and wherein a gas attachment is arranged between an attachment and the connection element.

* * * * *